United States Patent [19]

Inouye et al.

[11] Patent Number: 5,780,269

[45] Date of Patent: *Jul. 14, 1998

[54] HYBRID MOLECULES

[75] Inventors: Sumiko Inouye; Masayori Inouye, both of Bridgewater, N.J.

[73] Assignee: The University of Medicine and Denistry of New Jersey, Newark, N.J.

[*] Notice: The term of this patent shall not extend beyond the expiration date of Pat. No. 5,436,141.

[21] Appl. No.: 503,730

[22] Filed: Jul. 18, 1995

Related U.S. Application Data

[63] Continuation-in-part of Ser. No. 817,430, Jan. 6, 1992, Pat. No. 5,434,070, which is a continuation-in-part of Ser. No. 315,427, Feb. 24, 1989, Pat. No. 5,079,151, which is a continuation-in-part of Ser. No. 315,316, Feb. 24, 1989, Pat. No. 5,320,958, which is a continuation-in-part of Ser. No. 315,432, Feb. 24, 1989, abandoned, which is a continuation-in-part of Ser. No. 517,946, May 2, 1990, abandoned, which is a continuation-in-part of Ser. No. 518,749, Mar. 2, 1990, Pat. No. 5,405,775, which is a continuation-in-part of Ser. No. 753,110, Aug. 30, 1990, Pat. No. 5,436,141.

[51] Int. Cl.$^6$ ............................ C12P 19/34; C12N 15/74
[52] U.S. Cl. ........................ 435/91.1; 536/23.1; 536/25.2
[58] Field of Search ........................ 435/91.1, 240.2, 435/252.33, 254.21; 536/25.2, 23.1

[56] References Cited

U.S. PATENT DOCUMENTS

| | | | |
|---|---|---|---|
| 5,405,775 | 4/1995 | Inouye et al. | 435/252.33 |
| 5,436,141 | 7/1995 | Miyata et al. | 435/91.1 |

OTHER PUBLICATIONS

Mirochnitchenko, O. et al., *The Journal of Biological Chemistry*, 269:(28)2380–2383.
ATCC Catalogue of Bacteria & Bacteriophages 17th Edition 1989, American Type Culture Collection, p. 149.
Deutscher, M. P., et al., *Chemical Abstracts*, vol. 81, Abstract 10596 (1974).
Dhundale, A. et al., *Cell*, 51:1105–1112 (1987).
Dhundale, A. et al., *Journal of Bacteriology*, vol. 164, No. 2, pp. 914–917 (1985).
Dhundale, A. et al., *Journal of Bacteriology*, vol. 170, No. 12, pp. 5620–5624 (1988).
Dhundale, A. et al., *Journal of Biological Chemistry*, vol. 263, No. 18, pp. 9055–9058 (1988).
Lim, Dongbin et al., *Cell*, vol. 56 (1989).
Furuichi, et al., *Cell*, 48:47–53 (1987).
Furuichi, et al., *Cell*, 48:55–62 (1987).
Geider, K., et al., *Chemical Abstracts*, vol. 75, Abstract 126881 (1971).
Geider, K. et al., *Eur. J. Biochem.*, 21:374–384 (1971).
Hilderman, R. H., et al., *Chemical Abstracts*, vol. 85, Abstract 75812 (1976).
Hilderman, R. H. et al., *Archiv. Biochem. Biophys.*, 175:534–540 11 (1976).
Hsu, M. Y. et al., *J. Biol. Chem.*, 264:(11)6214–6219 (1989).
Inouye, Masayori et al., *Annu. Rev. Microbiol.*, vol. 45 (1991).
Inouye, Masayori et al., *TIBS 16*, 16:18–21 (1991).
Inouye, Sumiko et al., *Biochemistry*, vol. 87 (1990).
Inouye, Sumiko et al., *Science*, vol. 2 (1991).
Lampson, Bert C. et al., *Nucleic Acid Research and Molecular Biology*, vol. 40, 1991.
Lampson, Bert C. et al., *Science*, vol. 243, (1989).
Lampson, Bert C. et al., *Journal of Bacteriology*, vol. 173, No. 17 (1991).
Lim D. et al., *Cell*, 56:891–904 (1989).
Moses, R. E. et al., *Chemical Abstracts*, vol. 74, Abstract 29189 (1971).
Moses, R. E. et al., *Proc. Nat. Acad. Sci. USA*, 67:674–681 (1970).
Peterson, R. L. et al., *J. Bacteriol.*, 107:585–588 (1971).
Peterson, R. L. et al., *Chemical Abstracts*, vol. 75, Abstract 72923 (1971).
Sun, Jing et al., *Microbiology*, vol. 86 (1989).
Sun, Jing et al., *Journal of Bio. Chem.*, vol. 173, No. 13 (1991).
Viswanathan, Manickam et al., *The Journal of Bio. Chem.*, vol. 264, No. 23 (1989).
Yee, et al., *Cell*, 38:203–209 (1984).

*Primary Examiner*—James Ketter
*Attorney, Agent, or Firm*—Weiser and Associates P.C.

[57] ABSTRACT

Novel hybrid molecules comprising an RNA and a DNA portion are disclosed. A method for synthesizing the molecule is disclosed.

28 Claims, 21 Drawing Sheets

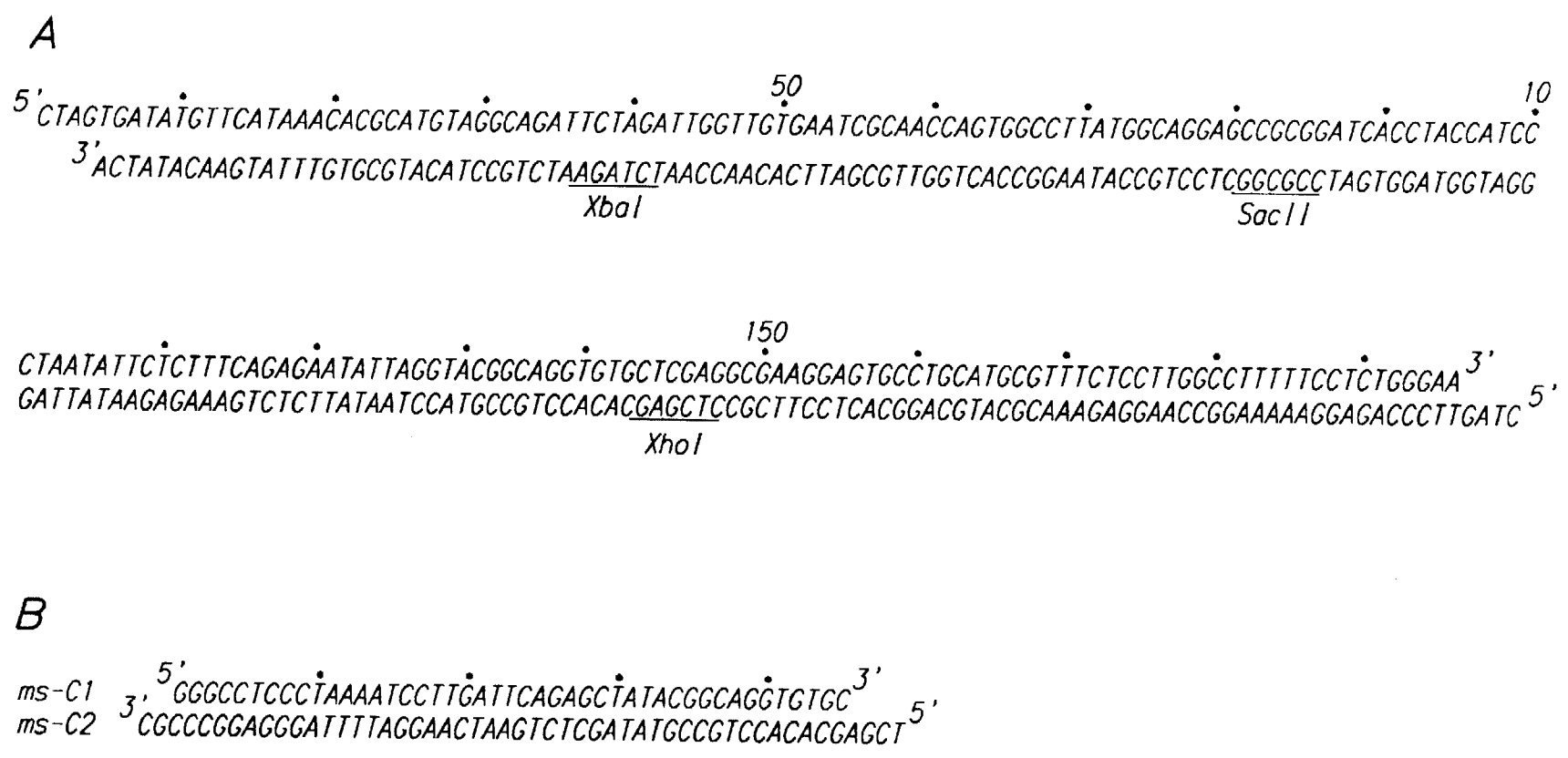

A

5' CTAGTGATATGTTCATAAACACGGATGTAGGCAGATTCTAGATTGGTTGTGAATCGCAACCAGTGGCCTTATGGCAGGAGCCCGGATCACCTACCATCC
3' ACTATACAAGTATTTGTGCCTACATCCGTCTAAGATCTAACCAACACTTAGCGTTGGTCACCGGAATACCGTCCTGGGCGCCTAGTGGATGGTAGG
                                                            Xbal                                    SacII CTAATATTCTCTTTCAGAGAATATTAGGTACGGCAGGTGTCTCCAGGCGAAGGAGTGCCTGCATGCGTTCTCCTTGGCCTTTTCCTCTGGAA 3'
GATTATAAGAGAAAGTCTCTTATAATCCATGCCGTCCACAGAGGTCCGCTTCCTCACGGACGTACGCAAGAGGAACCGGAAAAAGGAGACCCTTGATC 5'
                                    XhoI B
ms-C1   5' GGGCCTCCCTAAAATCCTTGATTCAGAGCTATACGGGCAGGTGTGC 3'
ms-C2   3' CGCCCGGAGGGATTTTAGGAACTAAGTCTCGATATGCCGTCCACACGAGCT 5'

FIG. 9B

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: both ( x i ) SEQUENCE DESCRIPTION: SEQ ID NO:1:

```
CACGCAUGUA  GGCAGAUUUG  UUGGUUGUGA  AUCGCAACCA  GUGGCCUUAA  UGGCAGGA                58
```

( 2 ) INFORMATION FOR SEQ ID NO:2:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: both ( x i ) SEQUENCE DESCRIPTION: SEQ ID NO:2:

```
TCCTTCGCAC  AGCACACCTG  CCGTATAGCT  CTGAATCAAG  GATTTAGGG  AGGCGATTCC                60

TCCTGCC                                                                              67
```

( 2 ) INFORMATION FOR SEQ ID NO:3:

( i ) SEQUENCE CHARACTERISTICS:
    ( A ) LENGTH: 132 base pairs
    ( B ) TYPE: nucleic acid
    ( C ) STRANDEDNESS: single
    ( D ) TOPOLOGY: both ( i x ) FEATURE:
    ( A ) NAME/KEY: misc_feature
    ( B ) LOCATION: 118
    ( D ) OTHER INFORMATION: /note= "mut-1, A to U"

( i x ) FEATURE:
    ( A ) NAME/KEY: misc_feature
    ( B ) LOCATION: 118
    ( D ) OTHER INFORMATION: /note= "mut-2, A to G"

( i x ) FEATURE:
    ( A ) NAME/KEY: misc_feature
    ( B ) LOCATION: 25
    ( D ) OTHER INFORMATION: /note= "mut-3, G to A"

( i x ) FEATURE:
    ( A ) NAME/KEY: misc_feature
    ( B ) LOCATION: 119
    ( D ) OTHER INFORMATION: /note= "mut-4, G to A"

( x i ) SEQUENCE DESCRIPTION: SEQ ID NO:3:

```
CACGCAUGUA  GGCAGAUUUG  UUGGUUGUGA  AUCGCAACCA  GUGGCCUUAA  UGGCAGGAGG     60
AAUCGCCUCC  CUAAAAUCCU  UGAUUCAGAG  CUAUACGGCA  GGUGUGCUGU  GCGAAGGAGU    120
GCCUGCAUGC  GU                                                            132
```

( 2 ) INFORMATION FOR SEQ ID NO:4:

( i ) SEQUENCE CHARACTERISTICS:
    ( A ) LENGTH: 49 base pairs
    ( B ) TYPE: nucleic acid
    ( C ) STRANDEDNESS: single
    ( D ) TOPOLOGY: both ( x i ) SEQUENCE DESCRIPTION: SEQ ID NO:4:

```
UGAGCCAUGA  GUACCGCGGU  GUUUCGCCGC  GGGGGUGUUC  UGUCCCAU                   49
```

( 2 ) INFORMATION FOR SEQ ID NO:5:

( i ) SEQUENCE CHARACTERISTICS:
    ( A ) LENGTH: 65 base pairs
    ( B ) TYPE: nucleic acid
    ( C ) STRANDEDNESS: single
    ( D ) TOPOLOGY: both ( x i ) SEQUENCE DESCRIPTION: SEQ ID NO:5:

```
CTGCGAGGCG  TTGGACCCGG  GGCTCCCTGC  GTTGCGTACG  CTGGGACCCT  GGCGAAGAGA     60
TGGGG                                                                     65
```

( 2 ) INFORMATION FOR SEQ ID NO:6:

( i ) SEQUENCE CHARACTERISTICS:
    ( A ) LENGTH: 58 base pairs
    ( B ) TYPE: nucleic acid
    ( C ) STRANDEDNESS: single
    ( D ) TOPOLOGY: both ( x i ) SEQUENCE DESCRIPTION: SEQ ID NO:6:

```
CACGCAUGUA  GGCAGAUUUG  UUGGUUGUGA  AUCGCAACCA  GUGGCCUUAA  UGGCAGGA       58
```

( 2 ) INFORMATION FOR SEQ ID NO:7:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: both ( x i ) SEQUENCE DESCRIPTION: SEQ ID NO:7:

```
TCCTTCGCAC   AGCACACCTG   CCGTATAGCT   CTGAATCAAG   GATTTAGGG   AGGCGATTCC        60
TCCTGCC                                                                          67
```

( 2 ) INFORMATION FOR SEQ ID NO:8:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: both ( x i ) SEQUENCE DESCRIPTION: SEQ ID NO:8:

```
AUGCGCACCC   UUAGCGAGAG   GUUUAUCAUU   AAGGUCAACC   UCUGGAUGUU   GUUUCGGCAU       60
CCUGCAUUGA   AUCUGAGUUA   CU                                                     82
```

( 2 ) INFORMATION FOR SEQ ID NO:9:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: both ( x i ) SEQUENCE DESCRIPTION: SEQ ID NO:9:

```
GTCAGAAAAA   ACGGGTTTCC   TGGTTGGCTC   GGAGAGCATC   AGGCGATGCT   CTCCGTTCCA       60
ACAAGGAAAA   CAGACAGTAA   CTCAGA                                                 86
```

( 2 ) INFORMATION FOR SEQ ID NO:10:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: both ( x i ) SEQUENCE DESCRIPTION: SEQ ID NO:10:

```
CAGAGCCAAA   CCUAGCAUUU   UAUGGGUUAA   UAGCCCAUCG   CCCAUGAGUC   AUGGUUUCGC       60
CUAGUAUUUU   AGCUA                                                               75
```

( 2 ) INFORMATION FOR SEQ ID NO:11:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: both ( x i ) SEQUENCE DESCRIPTION: SEQ ID NO:11:

```
TTGAGCACGT   CGATCAGTTC   GCTGATCGGT   GGCCCCAGC    CGCCGCTCAG   CGAACTGAAC       60
GACGGGCATA   GCT                                                                 73
```

( 2 ) INFORMATION FOR SEQ ID NO:12:

( i ) SEQUENCE CHARACTERISTICS:
        ( A ) LENGTH: 75 base pairs
        ( B ) TYPE: nucleic acid ( C ) STRANDEDNESS: single
( D ) TOPOLOGY: both ( x i ) SEQUENCE DESCRIPTION: SEQ ID NO:12:

| | | | | | |
|---|---|---|---|---|---|
| CGCCAGCAGU | GGCAAUAGCG | UUUCCGGCCU | UUUGUGCCGG | GAGGGUCGGC | GAGUCGCUGA | 60 |
| CUUAACGCCA | GUAGU | | | | | 75 |

( 2 ) INFORMATION FOR SEQ ID NO:13:

( i ) SEQUENCE CHARACTERISTICS:
        ( A ) LENGTH: 107 base pairs
        ( B ) TYPE: nucleic acid
        ( C ) STRANDEDNESS: single
        ( D ) TOPOLOGY: both ( x i ) SEQUENCE DESCRIPTION: SEQ ID NO:13:

| | | | | | |
|---|---|---|---|---|---|
| CATTAAACCA | TCCCGAAGGC | GCGTAACTGT | ACTGAGCGCG | TCAGCGCGAC | GTACGCGAAG | 60 |
| CGTACTCAGG | TACAAATGAG | CGAGTTTGGG | TATATGGACA | TACTACT | | 107 |

( 2 ) INFORMATION FOR SEQ ID NO:14:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: both ( x i ) SEQUENCE DESCRIPTION: SEQ ID NO:14:

| | | | | | |
|---|---|---|---|---|---|
| AGAGGUCCGG | AGUGCAUCAG | CCUGAGCGCC | UCGAGCGGCG | GAGCGGCGUU | GCGCCGCUCC | 60 |
| GGUUGGAAUG | CAGGACA | | | | | 77 |

( 2 ) INFORMATION FOR SEQ ID NO:15:

( i ) SEQUENCE CHARACTERISTICS:
        ( A ) LENGTH: 162 base pairs
        ( B ) TYPE: nucleic acid
        ( C ) STRANDEDNESS: single
        ( D ) TOPOLOGY: both ( x i ) SEQUENCE DESCRIPTION: SEQ ID NO:15:

| | | | | | |
|---|---|---|---|---|---|
| CATCTTACCT | GGGGCACGGT | AGCCTCACCG | GCTCTCCCCT | CCTAGGCACT | ACGGCCGGGG | 60 |
| TGGGTAAACG | GCGGTCGCGT | CGTTGGCTCC | GCTACCCACC | CTGGCCGTAG | TGCCTAGGAG | 120 |
| GGAGAGAGCC | AAGAACAGGC | TACCTTGCGG | AGAGTGTCCT | GC | | 162 |

( 2 ) INFORMATION FOR SEQ ID NO:16:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: both ( x i ) SEQUENCE DESCRIPTION: SEQ ID NO:16:

| | | | | | |
|---|---|---|---|---|---|
| AGAGGUCCCA | AGCCAUCAGC | CUCAGCGCCU | CGAGCGCGAG | AGCGGCGUUG | CGCCGCUCUG | 60 |
| GUUGAAUUGC | AGGACA | | | | | 76 |

( 2 ) INFORMATION FOR SEQ ID NO:17:

( i ) SEQUENCE CHARACTERISTICS:
        ( A ) LENGTH: 163 base pairs
        ( B ) TYPE: nucleic acid
        ( C ) STRANDEDNESS: single
        ( D ) TOPOLOGY: both ( x i ) SEQUENCE DESCRIPTION: SEQ ID NO:17:

| | | | | | |
|---|---|---|---|---|---|
| CTTCTCACCT | GGGGCACGGT | AGCCTCACCG | GCTCTCCCCT | CCGGTGAGTA | CCTCTCCGGC | 60
| CGGGGAAACG | GCGGTTGCGT | CGTTGGTTCA | GCTCCCCGGC | CGGAGAGGTA | CTCACCGGAG | 120
| GGAAGAGAGC | CAAGAACAGG | CTACCTTGCG | GAGAGTGTCC | TGC | | 163

( 2 ) INFORMATION FOR SEQ ID NO:18:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: both ( x i ) SEQUENCE DESCRIPTION: SEQ ID NO:18:

| | | | | | |
|---|---|---|---|---|---|
| CACGCAUGUA | GGCAGAUUUG | UUGGUUGUGA | AUCGCAACCA | GUGGCCUUAA | UGGCAGGA | 58

( 2 ) INFORMATION FOR SEQ ID NO:19:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: both ( x i ) SEQUENCE DESCRIPTION: SEQ ID NO:19:

| | | | | | |
|---|---|---|---|---|---|
| TCCTTCGCAC | AGCACACCTG | CCGTATAGCT | CTGAATCAAG | GATTTAGGG | AGGCGATTCC | 60
| TCCTGCC | | | | | | 67

( 2 ) INFORMATION FOR SEQ ID NO:20:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: both ( x i ) SEQUENCE DESCRIPTION: SEQ ID NO:20:

| | | | | | |
|---|---|---|---|---|---|
| CCAAACCUAG | CAUUUUAUGG | GUUAAUAGCC | CAUCGCGCAU | GAGUCAUGGU | UUCGCCUAGU | 60
| AUUUUAGCUA | | | | | | 70

( 2 ) INFORMATION FOR SEQ ID NO:21:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: both ( x i ) SEQUENCE DESCRIPTION: SEQ ID NO:21:

| | | | | | |
|---|---|---|---|---|---|
| TTGAGCACGT | CGATCAGTTC | GCTGATCGGT | GGCCCCCAG | CCGCCGCTCA | GCGAATTGAA | 60
| CGACGGGCAT | AGCT | | | | | 74

( 2 ) INFORMATION FOR SEQ ID NO:22:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: both ( x i ) SEQUENCE DESCRIPTION: SEQ ID NO:22:

| | | | | | |
|---|---|---|---|---|---|
| CACGCAUGUA | GGCAGAUUCU | AGAUUGGUUG | UGAAUCGCAA | CCAGUGGCCU | UAUGGCAGGA | 60

( 2 ) INFORMATION FOR SEQ ID NO:23:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: both ( x i ) SEQUENCE DESCRIPTION: SEQ ID NO:23:

```
TCCTTCGCCT CGAGCACACC TGCCGTACCT AATATTCTCT GAAAGAGAAT ATTAGGGATG    60
GTAGGTGATC CGCGGCTCCT GCC                                           83
```

( 2 ) INFORMATION FOR SEQ ID NO:24:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: both ( x i ) SEQUENCE DESCRIPTION: SEQ ID NO:24:

```
CACGCAUGUA GGCAGAUUCU AGAUUGGUUG UGAAUCGCAA CCAGUGGCCU UAUGGCAGGA    60
```

( 2 ) INFORMATION FOR SEQ ID NO:25:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: both ( x i ) SEQUENCE DESCRIPTION: SEQ ID NO:25:

```
TCCTTCGCCT CGAGCACACC TGCCGTATAG CTCTGAATCA AGGATTTTAG GGAGGCCCGC    60
GGCTCCTGCC                                                          70
```

( 2 ) INFORMATION FOR SEQ ID NO:26:

( i ) SEQUENCE CHARACTERISTICS:
        ( A ) LENGTH: 200 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:26:

```
CTAGTGATAT GTTCATAAAC ACGCATGTAG GCAGATTCTA GATTGGTTGT GAATCGCAAC    60
CAGTGGCCTT ATGGCAGGAG CCGCGGATCA CCTACCATCC CTAATATTCT CTTTCAGAGA   120
ATATTAGGTA CGGCAGGTGT GCTCGAGGCG AAGGAGTGCC TGCATGCGTT TCTCCTTGGC   180
CTTTTTCCTC TGGGAACTAG                                              200
```

( 2 ) INFORMATION FOR SEQ ID NO:27:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:27:

```
GCGGGCCTCC CTAAAATCCT TGATTCAGAG CTATACGGCA GGTGTGCTCG A            51
```

( 2 ) INFORMATION FOR SEQ ID NO:28:

( i ) SEQUENCE CHARACTERISTICS:
        ( A ) LENGTH: 30 base pairs
        ( B ) TYPE: nucleic acid ( C ) STRANDEDNESS: single
( D ) TOPOLOGY: both ( x i ) SEQUENCE DESCRIPTION: SEQ ID NO:28:

TTGAGCACGT CGATAACGAC GGGCATAGCT    30

( 2 ) INFORMATION FOR SEQ ID NO:29:

( i ) SEQUENCE CHARACTERISTICS:
( A ) LENGTH: 53 base pairs
( B ) TYPE: nucleic acid
( C ) STRANDEDNESS: single
( D ) TOPOLOGY: both ( x i ) SEQUENCE DESCRIPTION: SEQ ID NO:29:

TTGAGCACCA TGGTTTCATT ATTAATACCC TCTAGATTCC ATGGGGCATA GCT    53

( 2 ) INFORMATION FOR SEQ ID NO:30:

( i ) SEQUENCE CHARACTERISTICS:
( A ) LENGTH: 62 base pairs
( B ) TYPE: nucleic acid
( C ) STRANDEDNESS: single
( D ) TOPOLOGY: both ( x i ) SEQUENCE DESCRIPTION: SEQ ID NO:30:

TTGAGCACCA TGGTTTAGTA GCTGTCATTA TTAATACCCT CTAGATTCCA TGGGGCATAG    60

CT    62

( 2 ) INFORMATION FOR SEQ ID NO:31:

( i ) SEQUENCE CHARACTERISTICS:
( A ) LENGTH: 65 base pairs
( B ) TYPE: nucleic acid
( C ) STRANDEDNESS: single
( D ) TOPOLOGY: both ( x i ) SEQUENCE DESCRIPTION: SEQ ID NO:31:

TTGAGCACGT GAATTCCGCT TTCATTATTA ATACCCTCTA GATTGCGGAA TTCACGGGCA    60

TAGCT    65

( 2 ) INFORMATION FOR SEQ ID NO:32:

( i ) SEQUENCE CHARACTERISTICS:
( A ) LENGTH: 59 base pairs
( B ) TYPE: nucleic acid
( C ) STRANDEDNESS: single
( D ) TOPOLOGY: linear ( x i ) SEQUENCE DESCRIPTION: SEQ ID NO:32:

GCUACAUGGA GAAUUAACUC AAUCUAGAGG GUAUUAAUAA UGAAAGCUAC UAAACUGGU    59

( 2 ) INFORMATION FOR SEQ ID NO:33:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:33:

TTTAGTAGCT TTCATTATTA ATACCCTCTA GATT    34

( 2 ) INFORMATION FOR SEQ ID NO:34:

( i ) SEQUENCE CHARACTERISTICS:

(A) LENGTH: 55 base pairs
(B) TYPE: nucleic acid
(C) STRANDEDNESS: single
(D) TOPOLOGY: both (xi) SEQUENCE DESCRIPTION: SEQ ID NO:34:

CACGCAUGUA GGCAGAUUCU AGAUUGGUUG UGCAACCAGU GGCCUUAUGG CAGGA    55

(2) INFORMATION FOR SEQ ID NO:35:

(i) SEQUENCE CHARACTERISTICS:
  (A) LENGTH: 80 base pairs
  (B) TYPE: nucleic acid
  (C) STRANDEDNESS: single
  (D) TOPOLOGY: both (xi) SEQUENCE DESCRIPTION: SEQ ID NO:35:

TCCTTCGCCT CGAGCACACC TGCCGTACCT AATATTCTCT AGAGAATATT AGGGATGGTA    60

GGTGATCCGC GGCTCCTGCC    80

(2) INFORMATION FOR SEQ ID NO:36:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (xi) SEQUENCE DESCRIPTION: SEQ ID NO:36:

ATCCCTGGCA GTTCC    15

(2) INFORMATION FOR SEQ ID NO:37:

(i) SEQUENCE CHARACTERISTICS:
  (A) LENGTH: 50 base pairs
  (B) TYPE: nucleic acid
  (C) STRANDEDNESS: single
  (D) TOPOLOGY: linear (xi) SEQUENCE DESCRIPTION: SEQ ID NO:37:

CGGTAAAACC TCCCACCTGC GTGCTCACCT GCGTTGGCAC ACCGGTGAAA    50

(2) INFORMATION FOR SEQ ID NO:38:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (xi) SEQUENCE DESCRIPTION: SEQ ID NO:38:

TTTCACCGGT GTGCCAA    17

(2) INFORMATION FOR SEQ ID NO:39:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (xi) SEQUENCE DESCRIPTION: SEQ ID NO:39:

TGCGAAGGTG TGCCTGCA    18

(2) INFORMATION FOR SEQ ID NO:40:

(i) SEQUENCE CHARACTERISTICS:

( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:40:

TGCGAAGGGG TGCCTGCA                                                                                18

( 2 ) INFORMATION FOR SEQ ID NO:41:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:41:

ATGTAGGCAA ATTTGTTGG                                                                               19

( 2 ) INFORMATION FOR SEQ ID NO:42:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:42:

TGCGAAGGAA TGCCTGCAT                                                                               19

( 2 ) INFORMATION FOR SEQ ID NO:43:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:43:

AATCTAGACA GAGCCAAACC TAG                                                                          23

( 2 ) INFORMATION FOR SEQ ID NO:44:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:44:

TACTTGAGCA CCATGGGGCA TAGCTAA                                                                      27

( 2 ) INFORMATION FOR SEQ ID NO:45:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:45:

TCTCTAGATC CTTATGCACC TTGA                                                                         24

HYBRID MOLECULES

RELATED CASES

This application is a continuation-in-part of U.S. patent application Ser. No. 07/817,430, filed Jan. 6, 1992 now U.S. Pat. No. 5,434,070; which is a continuation-in-part of U.S. patent application Ser. No. 07/315,427, filed Feb. 24, 1989 which issued as U.S. Pat. No. 5,079,151; which is a continuation-in-part of U.S. patent application Ser. No. 07/315,316, filed Feb. 24, 1989 now U.S Pat. No. 5,320,958; which is a continuation-in-part of U.S. patent application Ser. No. 07/315,432, filed Feb. 24, 1989 now abandoned; which is a continuation-in-part of U.S. patent application Ser. No. 07/517,946, filed May 2, 1990 now abandoned; which is a continuation-in-part of U.S. patent application Ser. No. 07/518,749, filed Mar. 2, 1990 now U.S. Pat. No. 5,405,775; which is a continuation-in-part of U.S. patent application Ser. No. 07/753,110, filed Aug. 30, 1991 now U.S. Pat. No. 5,436,144.

FIELD OF THE INVENTION

This invention relates to the field of recombinant DNA. More particularly, the invention relates in a generic manner to a unique and unusual genetic structure, a multi-copy single-stranded DNA/RNA hybrid structure, herein designated as msDNAs. The invention also relates to reverse transcriptases (RT) which are capable of synthesizing a cDNA molecule from an RNA template in a unique manner. The invention also relates to a free-cell synthesis of msDNAs with the RTs.

BACKGROUND OF THE INVENTION

Individual species of msDNAs and reverse transcriptases essential for their synthesis have been discussed in our pending patent applications, and in our publications. We have discovered that not withstanding the great diversity of these msDNA species, msDNAs share essential, common and conserved structural and functional elements. The invention therefore relates to such DNAs whether known, individual species discussed in our earlier patent applications or other msDNAs to be identified in the future to the extent that they share in these common features.

Until recently it had been commonly believed that retroelements which encode RTs are exclusively found in eukaryotes and that bacterial populations do not contain retroelements. The finding of retroelements in prokaryotes, the requirement of reverse transcriptase (RT) for msDNA synthesis has raised fundamental scientific questions regarding the possible origin and evolution of the retroelement encoding the reverse transcriptase RT, molecular mechanisms of msDNA synthesis, and the functions of msDNAs in cells.

Novel findings have also been made regarding a possible mechanism of synthesis of the msDNAs by RTs. Thus, the studies carried out and associated discoveries have important scientific significance.

The msDNAs have important utilities, as described hereinafter. These structures are therefore also significant from the practical point of view in molecular biology, medical, immunology and other applications.

United States patent applications relating to various msDNAs and RTs are the following:

Ser. No. 07/315,427 discloses a method for synthesizing various msDNAs in vitro. By this method a variety of synthetic msDNAs can be prepared in an efficient and practical manner. Ser. No. 07/315,316 discloses an msDNA molecule from a prokaryote, *M. xanthus*. This was a particularly noteworthy breakthrough in this series of discoveries. Ser. No. 07/315,432 discloses an msDNA molecule from another prokaryote, *E. coli*. This invention contributed to the generic finding of msDNA structures whose synthesis is dependent on RT in prokaryotes. Ser. No. 07/517,946 discloses prokaryote msDNAs synthesized from DNA fragments designated as retrons. Ser. No. 07/518,749 discloses further msDNA molecules synthesized from recombinant DNA constructs, designated as retrons. Ser. No. 07/753,110 discloses a large variety of msDNAs synthesized in vivo in eukaryotic organisms such as yeast, plant cells and mammalian cells.

For background art, one skilled in the art may refer to Dhundale, *Cell*, 51, pp. 1105–1112 (1987); Weiner et al., *Ann. Rev. Biochem*, 55, pp. 631–661 (1986); Yee et al., *Cell*, 38, pp. 203–209(1984); and Lim and Maas, *Cell*, 56, 891–904 (Mar. 10, 1989). Other background references of interest may be found in the above referred to patent applications and are cited in the REFERENCES pages of this application.

RELATED PATENT APPLICATIONS

This is a continuation-in-part of allowed U.S. application Ser. No. 07/315,427, filed Feb. 24, 1989, entitled "The Use of Reverse Transcriptase to Synthesize Branched-RNA Linked Multi-Copy Single-Stranded DNA", by Bert C. Lampson, Masayori and Sumiko Inouye; and of pending U.S. applications Ser. Nos. 07/315,316, filed Feb. 24, 1989, entitled "Reverse Transcriptase from Myxobacteria", by Masayori and Sumiko Inouye, Mei-Yin Hsu, Susan Eagle; 07/315,432, filed Feb. 24, 1989, entitled "Reverse Transcriptase from *E. Coli*", by Bert C. Lampson, Jing Sun, Mei-Yin Hsu, Jorge Vallejo-Ramirez, Masayori and Suriko Inouye; also of 07/517,946, filed May 2, 1990 entitled "Prokaryotic Reverse Transcriptase, by Masayori and Sumiko Inouye, Bert C. Lampson, Mei-Yin Hsu, Susan Eagle, Jing Sun, Jorge Vallejo-Ramirez; 07/518,749 filed May 2, 1990, entitled "*E. coli* msDNA Synthesizing System, Products and Uses", by Masayori and Sumiko Inouye; also of 07/753,110 filed Aug. 30, 1991, entitled "Method for Synthesizing Stable Single-Stranded cDNA in Eukaryotes Means of a Bacterial Retron, Products and Uses Therefor", by Shohei Miyata, Atsushi Ohshima, Masayori and Sumiko Inouye. These applications are incorporated herein by reference.

Dhundale et al. referred to above, speculate about a possible synthesis mechanism for the synthesis of msDNA. The publication discusses a nucleotide fragment which is presumed to encode msDNA. Although the fragment contains portions of the elements necessary to code for msDNA, it does not contain an open reading frame to code for a reverse transcriptase (RT) which is necessary for the synthesis of msDNA.

The present invention incorporates earlier disclosures in U.S. pending patent applications Ser. No. 07/315,427 filed Feb. 24, 1989 entitled "Production of Branched RNA-linked Multi-copy Single-Stranded DNA using Permeabilized Cells" and other applications identified above. In these three first applications, there is disclosed all the DNA and RNA elements necessary to code for the entire msDNA molecule including the open reading frame which codes for the reverse transcriptase (RT) and when present, the ribonuclease H (RNase H) domains.

The discovery of the location of the open reading frame in the same DNA fragment as the gene encoding the RNA and DNA portion of the final msDNA molecule could not be foreseen at that time. This observation is further supported by a recent publication of independent researchers, Lease and Yee in *JBC*, 266, 14497–14503 (August 1991) entitled "Early Events in the Synthesis of the Multicopy Single-stranded DNA-RNA Branched Copolymer of *Myxococcus xanthus*". The authors question that a reverse transcriptase alone, by itself, was sufficient to completely and directly synthesize msDNA on an RNA template. They propose an alternative model for the synthesis of msDNA. They propose a synthesis in which a single-stranded DNA corresponding to the DNA portion of the msDNA is first synthesized in a conventional manner by a 3' to 5' priming reaction; this DNA strand is then ligated to the 2'-OH group of the branched rG residue of msdRNA at its 5' end forming a 2',5'-phosphodiester linkage. In contrast, the disclosure in the earlier patent applications identified above and the disclosure made herein clearly exclude this alternative model. It was found that the synthesis of msDNA-Ec67 is primed de novo by a single dNTP base using an RNA precursor molecule. Furthermore, the first deoxynucleotide addition as well as the extension of the DNA strand from the first base is absolutely dependent upon the template RNA sequence and RT. It is undoubtedly appears that msDNA is synthesized directly on an RNA template by reverse transcriptase. The 5' end sequence of the msr-msd transcript (bases 1–113) forms a duplex with the 3' end sequence of the same transcript, thus serving as a primer as well as a template for msDNA synthesis by reverse transcriptase. It appears therefore that the reverse transcriptases with which the group of researchers named in the earlier patent applications and herein have been working is unique. The reverse transcriptases are essential and capable by themselves to synthesize each of the entire msDNA molecules. The synthesis is initiated by a novel 2',5'-branched priming event on the folded msr template in which a dT residue is linked to the 2'-OH of an internal rG residue of the msdRNA molecule. This is further described below.

SUMMARY OF THE INVENTION

The invention relates to three main embodiments. The generic features of msDNAs; RTs which have the ability to synthesize cDNA from a template by a unique 3',5'-priming event; and a cell-free system to synthesize msDNAs with such RTs.

The description of these embodiments presents two unprecedented aspects in molecular biology: first, the priming of cDNA synthesis from the 2'-OH group of an internal guanosine residue in the RNA strand and secondly, the existence of reverse transcriptase in procaryotes.

The invention encompasses broadly a DNA/RNA hybrid structure which comprises a single-stranded DNA portion linked with and forming an integral part with a single-stranded RNA portion, herein designated as msDNA. The msDNAs are produced in several hundred copies from a genetic element identified herein as a "retron", and are therefore identified as multicopy, single-stranded DNAs or msDNAs. A generic representation of common features of the msDNAs of the invention is shown below.

An important and valuable feature of the msDNAs is that notwithstanding their single-strandedness, their remarkable stability which makes them very well suited for several utilities. Of particular interest is the use of the msDNAs in antisense applications against the mRNA of a target gene encoding a protein, as will be described hereinafter.

It will be observed from the graphic generic representation of the common features of the msDNAs shown below that the msDNA is a molecule which is constituted of a stable hybrid branched RNA portion covalently linked to a single-strand DNA portion by a 2',5'-phosphodiester bond between the 2'-OH group of an internal rG residue and the 5'-phosphate of the DNA molecule, and non-covalently linked to the DNA by base pairing between the complementary 3' ends of the RNA and DNA molecules. In the msDNA molecule, RNA and DNA portions form one or more stable stem-and-loop secondary structures. The msDNAs are encoded by a single primary transcript, pre-msdRNA, which in turn is encoded by a genetic element called a retron. The retrons are genetic elements which contain a coding region msr for the RNA portion of the hybrid molecule and msd for the DNA portion of the msDNA molecule, respectively and an open reading frame (ORF). The pre-msdRNA likewise comprises the ORF, the msr and msd regions. Synthesis of the msDNAs require the transcription of the region encompassing the msr, msd regions and the ORF. However, the ORF and the msr-msd regions do not necessarily have to be present in the same transcriptional unit.

The generic structure of the msDNAs all possess this unique branched linkage forming the RNA and DNA strands. Further, the branched residue is in all cases, an internal guanosine residue in the 5' end of the RNA transcript.

Another conserved feature of the msDNAs is the base pairing of the 3' ends of the DNA and RNA portions. A further conserved feature that codes for the msDNAs is a set of inverted repeats (IR) sequences which are located as described hereinafter. The existence of the IRs is essential for the synthesis of the msDNA which contain the typical stem-loop structures. They allow the transcript RNA to fold into important secondary structures.

From the description herein, it is to be noted that the generic representation of the msDNA of the invention provides optional common secondary structures, like the stem-and-loop structure, which if present is part of the ssDNA portion of the molecule and at least one stem-and-loop structure is part of the ssRNA portion of the molecule. Further, the msDNAs of the invention, may have different nucleotide lengths, both with respect to their DNA and RNA portions. Other variables of the msDNAs will become apparent from the description that follows.

The invention also relates to RTs which are capable by themselves to synthesize the entire msDNA molecule from a template starting with a priming event which forms a unique 2',5'-linkage between the template molecule and the first nucleotide at the 5' end of the cDNA strand. The RT has interesting practical applications.

The invention also relates to a cell-free synthesis in which RT synthesizes cDNA from an RNA template and forms the entire msDNA structure. The cell-free system provides further confirmation of the unique property of the RTs.

DESCRIPTION OF THE FIGURES

FIG. 9b (Seq ID Nos. 26 and 27) shows genes and components of synthetic msDNA.

FIGS. 12a–12f (Seq. ID Nos. 10, 11, 28–33) show the structures of msDNA-Ec73 and its derivatives, and the antisense sequences used in the msDNAs.

FIG. 13 shows the production of msDNAs containing Anti-lpp sequences.

FIG. 14 shows the inhibition of lipoprotein production by Antisense DNA.

DESCRIPTION OF THE PREFERRED EMBODIMENTS

Figure 1A:
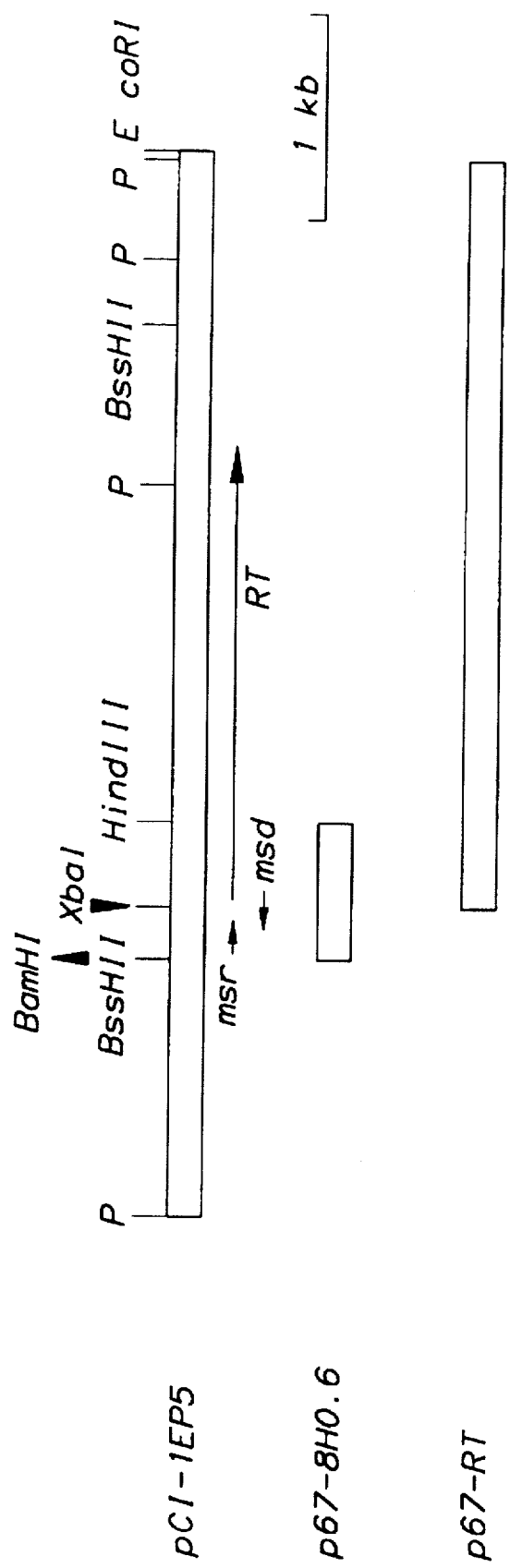
FIGS. 1A–1C show restriction map of pC1-1EP5, the proposed secondary structure of msDNA-Ec67 and a putative secondary structure of the precursor RNA molecule. Part A shows the restriction map of pC1-1EP5 (Lampson et al., 1989b). The BssHI site changed to a BamHI site is also shown by an arrowhead and the XbaI site created by site-specific mutagenesis is shown by an arrowhead. Locations and orientation of msr and msd and the RT gene are shown by arrows. The regions cloned into p67-BHO.6 and p67-RT are indicated by open boxes, respectively. Part B shows the structure of msDNA-Ec67 (Lampson et al., 1989b). The branched rG is circled and RNA is boxed. Both RNA (Seq ID NO.1) and DNA (Seq ID NO.2) are numbered from their 5'-ends. Part C shows a putative secondary structure of the precursor RNA molecule (Seq ID NO.3). The 5'-end of the RNA transcript was determined by primer extension (Hsu et al., unpublished results). The 3'-end of the RNA molecule is considered to form a stem structure using the inverted repeat sequence, a1 and a2 (arrows) in the primary RNA transcript (Lampson et al., 1989b). The branched rG is circled. Bases changed by mutations are indicated by arrows with individual designations. Open and filled triangles indicate the positions of the 3'-ends of RNA and DNA in msDNA-Ec67, respectively.

Generally, msDNA may be described as a molecule which comprises a branched single-stranded RNA portion which is covalently linked to a single-stranded DNA portion by a 2'-5'-phosphodiester bond between the 2'-OH group of a branched rG residue internal the RNA strand and the 5'-phosphate of the DNA molecule. Other common features are a non-covalently linked DNA-RNA hybrid at the 3' ends which is formed by base pairing between the complementary 3' ends of the DNA and RNA molecules and stable secondary structures in both the DNA and RNA strands.

The extreme 3' end of the DNA strand contains a sequence complementary to the sequence at the 3' end of the RNA strand. This allows the overlapping 3' ends of the DNA and RNA to form an RNA-DNA base-paired region. The presence of this short RNA-DNA hybrid is a result of the mechanism by which msDNA is synthesized via RT.

The msDNA molecule exists free of the chromosome in the cell cytoplasm, and can be isolated by the same methods used to isolate plasmids). msDNA is stable in spite of the fact that the molecule consists of single-stranded RNA and DNA portions. This stability is believed to result from the branched structure that protects the 5' end of the DNA, the RNA molecule after the branched G residue and the 3' end DNA-RNA hybrid. Analysis of msDNA molecules reveals a large degree of nucleotide sequence diversity among them, with little if any, primary sequence homology in either the DNA or RNA strand. However, in spite of their structural diversity, all msDNAs share important common primary and secondary structures in common, as described herein.

The msDNAs of the invention are encoded by genetic elements designated as retrons. The retrons comprise three distinct regions: an msr region which codes for the RNA portion of the msDNA, an msd region which codes for the DNA portion of the msDNA and an open reading frame (ORF) which codes for a polypeptide having reverse transcriptase (RT) activity. In one of the msDNAs (msDNA-Ec67), the ORF codes for an RT which has ribonuclease H (RNase H) activity. It is not excluded that other msDNAs yet to be discovered will also be synthesized by RTs which contain an RNase H domain. The above-discussed three elements can occur in a single operon or the msr-msd region can be separate from the RT gene yet operates in concert with the RT gene to synthesize the msDNAs. The msr-msd region and the msr-msd region and the RT gene can be expressed under the control of a single promoter or the RT can be expressed by a separate promoters.

Transcription of the msr and msd region yields a primary transcript, pre-msdRNA. This primary transcript encompasses all three regions: the msr, msd, and ORF regions of the retron, as is further described below.

The common features of msDNAs a) the 2',5'-phosphodiester linkage between a G residue within a continuous RNA strand, b) stable secondary structures in the RNA and DNA portions and c) the RNA-DNA hybrid structure at their 3' ends, may be seen below in Formula I (Seq ID Nos. 34 and 35).

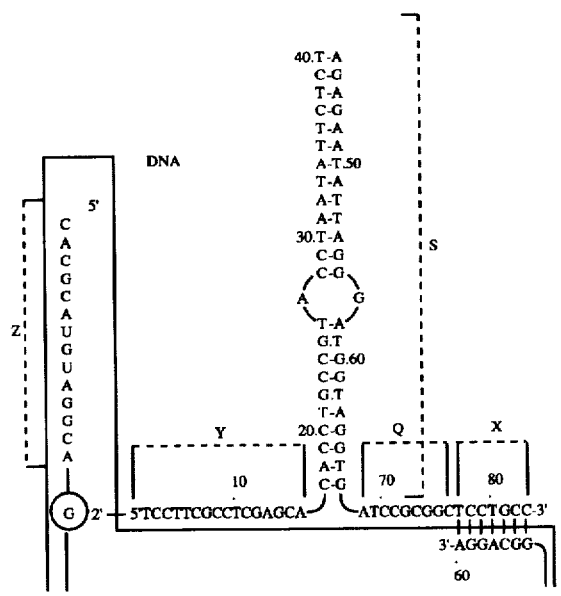

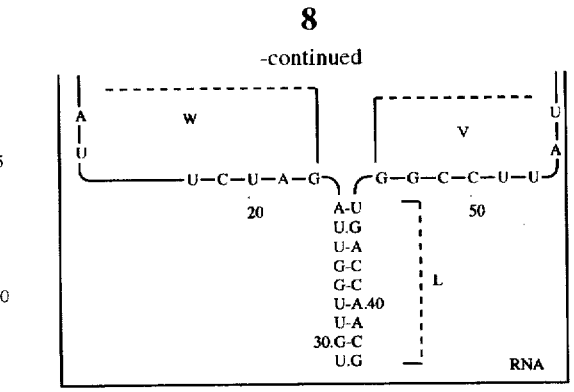

in which the following symbols have the following meanings:

X represents the overlapping 3' ends of the complementary bases of the DNA and RNA strands. Y represents the length of the 5' end of the DNA strand linked to the branched rG residue of the RNA portion defined from the first nucleotide that is not part of the stem of the stem-loop structure (not complementary to another base) to the last nucleotide of the 5' end. Z represents a portion of the stem of the stem-and-loop structure which includes the rG residue. S represents a portion of a typical stem-and-loop structure in the DNA portion. L represents a portion of a stem-and-loop structure of the RNA portion. W represents the length of the RNA strand from the internal rG residue to the first nucleotide of the stem-loop structure in the RNA portion of the molecule, i.e., to the first of such structures when more than one is present. $W_1$, $W_2$, $W_3$, etc. represents the length of the RNA strand between two consecutive stem-loop structures in the RNA portion, when more than one is present in the W portion of that strand. All lengths are determined in numbers of nucleotides. V represents the length of the RNA strand extending (or positioned) between the portion of complementary bases (X) and the first nucleotide of the stem (of the stem-loop in the RNA portion) between the first nucleotide of the stem-loop structure closest to the first complementary base in the 3' end of the RNA strand. All lengths are determined in numbers of nucleotides. Q represents the length of the DNA strand from the last complementary base (remote from the 3' end) in the DNA extending (or positioned) between the portion of complementary bases (X) at the 3' end and the first nucleotide of the stem (of the stem-loop in the DNA portion) to the first nucleotide of the first stem-loop structure in the DNA strand. $Q_1$, $Q_2$, $Q_3$, etc. represents the length of the strand between two consecutive stem-loop structures in the Q portion of the DNA strand of the molecule when more than one such structure is present in the Q portion of that strand. All lengths are determined in numbers of nucleotides.

All of the above lengths can vary considerably from one msDNA molecule to another.

The number of the stem-loop structures in the DNA and in the RNA portions may vary depending on the number of inverted repeats in the msd and the msr regions of the retron. However, their presence is not essential. To the extent that the IR may have non-complementary bases, this fact will be reflected in the stem portion of the respective stem-loop structure as shown in the Figures by a loop or non-pairing bases of the stem. There may be one or more such non-pairing loops.

The length of X may vary as described herein depending on the extent of overlap of the of the IR which constitutes the 3' end of the respective strands. Likewise, the length of Z and/or Y and/or L may vary considerably between individual msDNAs.

The length of X in number of nucleotides among known msDNAs ranges from 5 to 11. In Ec73, it is 5; in Mx65 and Ec107 it is 6; in Ec67, it is 7; in Mx162 and Sa163, it is 8 and in Ec86, it is 11. The length of X in number of nucleotides can also vary outside of the range stated above.

The length of Y in number of nucleotides among known msDNAs ranges from 7 to 69. In Ec73 and Ec107, Y is 7; in Mx162 and Sa163, Y is 13; in Ec86 it is 15; in Mx65 it is 16; and in Ec67 it is 19. The length of Y in number of nucleotides in Ye117 is 69.

It is contemplated that other msDNAs can have longer or shorter Ys provided the basic common conserved features are not adversely affected.

The number of stem-and-loop structures (S) in the DNA portion of known msDNAs is 1. The length of S in number of nucleotides varies among known msDNAs from 34 to 136. The length of S in number of nucleotides in Ec67 and Ye117 it is 34. In Mx65 it is 35; in Ec86 it is 53; in Ec73 it is 56; and in Ec107 it is 89. A the length of S in number of nucleotides in Mx162 and Sa163 is 136.

The number of stem-and-loop structures (L) in the RNA portion of the msDNAs of the invention is at least 1. The length of L in number of nucleotides ranges among the msDNAs of the invention from 9 to 26. In Ec86, the lengths are 9 and 18; in Mx65 it is 18; in Ec67 and Ye117 it is 26 nucleotides; in Mx162 and Sa163 they are 15 and 20; in Ec107 they are 20 and 20; and in Ec73 they are 10 and 15. It is contemplated that other msDNAs can have a greater number and/or different length stem-loop structures in the DNA and/or RNA portion.

The total number of nucleotides in the msDNAs may vary over quite a range. Presently in known msDNAs, the number of nucleotides ranges between 114 and 239. Likewise, the number of nucleotides of the RNA and the DNA portions varies between 49–82 and 65–163, respectively. The number of nucleotides of either or both portions can be varied, i.e., lengthened or shortened. Such larger or smaller msDNAs can be prepared from in vivo or in vitro synthesized msDNAs.

Illustrated herein are msDNAs as follows. Mx162 which has 162 DNA nucleotides and 77 RNA nucleotides; Mx65 which has 65 DNA nucleotides and 49 RNA nucleotides; Sa163 which has 163 DNA nucleotides and 76 RNA nucleotides; Ec67 which has 67 DNA nucleotides and 58 RNA nucleotides; Ec86 which has 86 DNA nucleotides and 82 RNA nucleotides; Ec73 which has 73 nucleotides and 75 RNA nucleotides; Ec107 which has 107 DNA nucleotides and 75 RNA nucleotides; msDNA-Ye which has a total of 175 nucleotides (117 DNA and 58 RNA); msDNA-100 which has a total of 143 nucleotides (83 DNA and 60 RNA); and msDNA 101 which has a total of 130 nucleotides (70 DNA and 60 RNA).

Another variable of the msDNAs is the overlap of complementary nucleotides of the DNA and RNA strands at their respective 3' ends which are non-covalently linked. The minimum number of overlapping complementary nucleotides found to date is 5 and the maximum is 11. For example, Ec73 has 5 overlapping bases. Mx65 and Ec107 have six. Ec67, msDNA-100, 101 and Ye117 have seven overlapping base-pairs. Mx162 and Sa163 have 8. Ec86 has 11.

With respect to the 5' end of the RNA strand, the lengths of the strands to the internal branched rG residue can also vary. The minimum number of residues counting from the 5' end of the RNA prior to the rG nucleotide residue found to date is 3 and the maximum is 19. The position of the branched G residue at the 5' end of the RNA strand is 4 from the 5' end for Mx65. For Ec86, the branched G residue is positioned at 14. For Ec67 and Ec73, the branched G residue is positioned at 15. For Ec107, the branched G residue is positioned at 18. For Sa163, the branched G residue is positioned at 19. And for Mx162, the branched G residue is positioned at 20. For msDNA-100, 101 and Ye117, the branched G residue is at residue 15.

With respect to the IR (a1 and a2), they too can vary in lengths. The minimum length of the repeat found to date is 12 and the maximum length is 34. The length of the inverted repeat in the retron of Ec86 is 12. For Ec67 and Ec73, the length is 13. The length in Mx65 is 15. The length in Ec107 is 16. And the lengths of the inverted repeats in Sa163 and Mx162 are 33 and 34, respectively.

Likewise, the distance between the msr-msd region and the ORF in various msDNAs can vary significantly. The minimum distance between the msd and ORF found to date is 19 and the maximum distance 77. For example, in msDNA-Ec86, 19 nucleotides separate the ORF from the msd. In Mx65, the distance is 28. For Ec107, the distance is 50. The number of separating nucleotides in Ec67 is 51. For Ec73, it is 53. For Mx162, 77 nucleotides separate the ORF from the msd.

For a listing of the variations of common features of the msDNAs of the invention, reference is made to Table 1.

Providing the essential functional components of the msDNAs are preserved, i.e., those that are essential for synthesis and uses of the msDNAs, the other components of the msDNAs can be varied as desired. Thus, insertions and/or deletions in the msr and/or msd regions or outside of the regions on the nucleotide sequence in which the retron is positioned, result in msDNAs variants which retain the common generic features.

As discussed below, for instance, insertions of nucleotide sequences at any site in the DNA and/or RNA portions (by appropriate insertions in the msd and/or msr genes) can produce very useful msDNAs that can serve as antisense vectors.

Figure 6A:
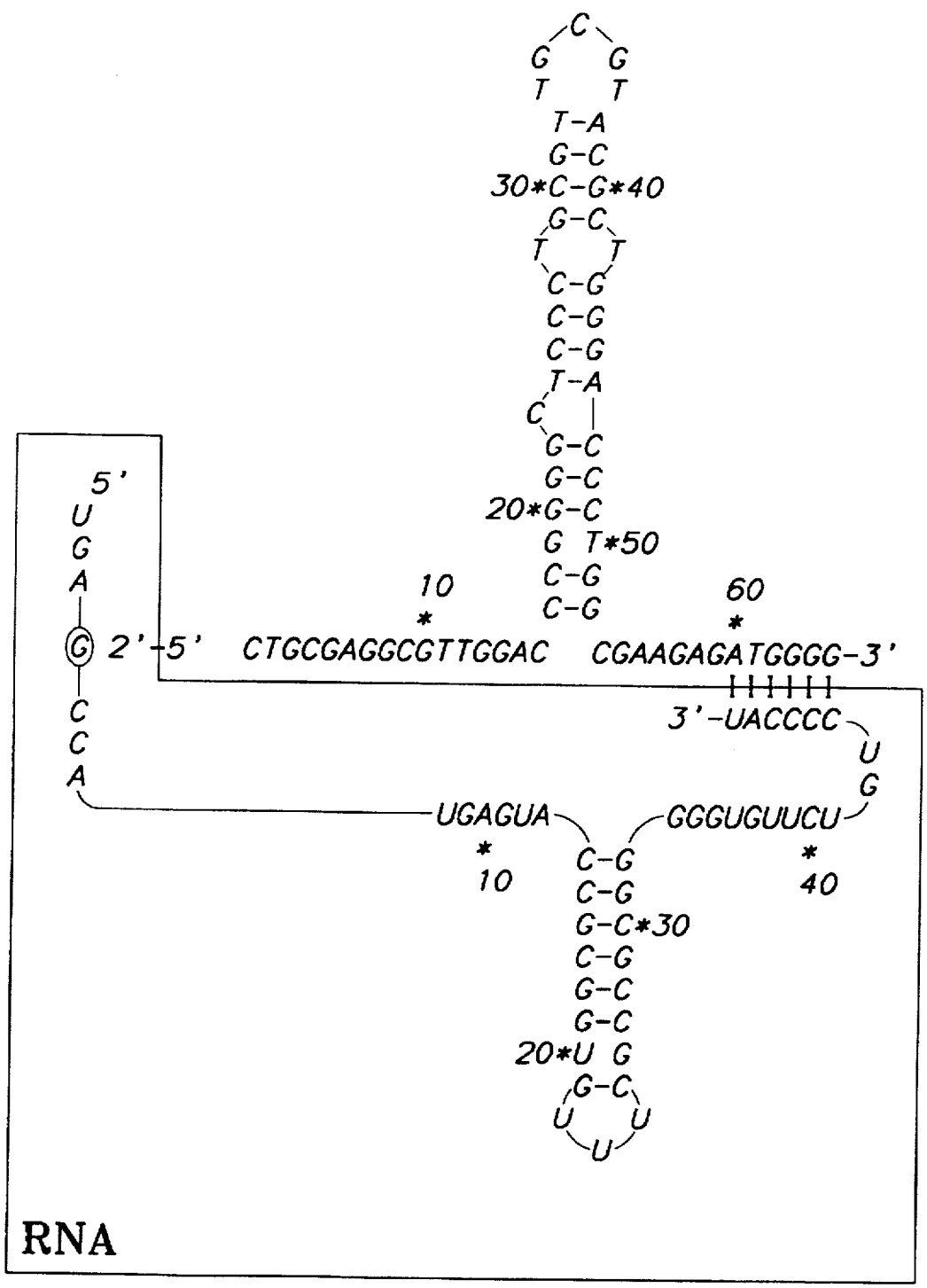
FIGS. 6a–6h show the complete nucleotide sequence of typical msDNAs (Seq ID Nos. 4–19).
Figure 6B:
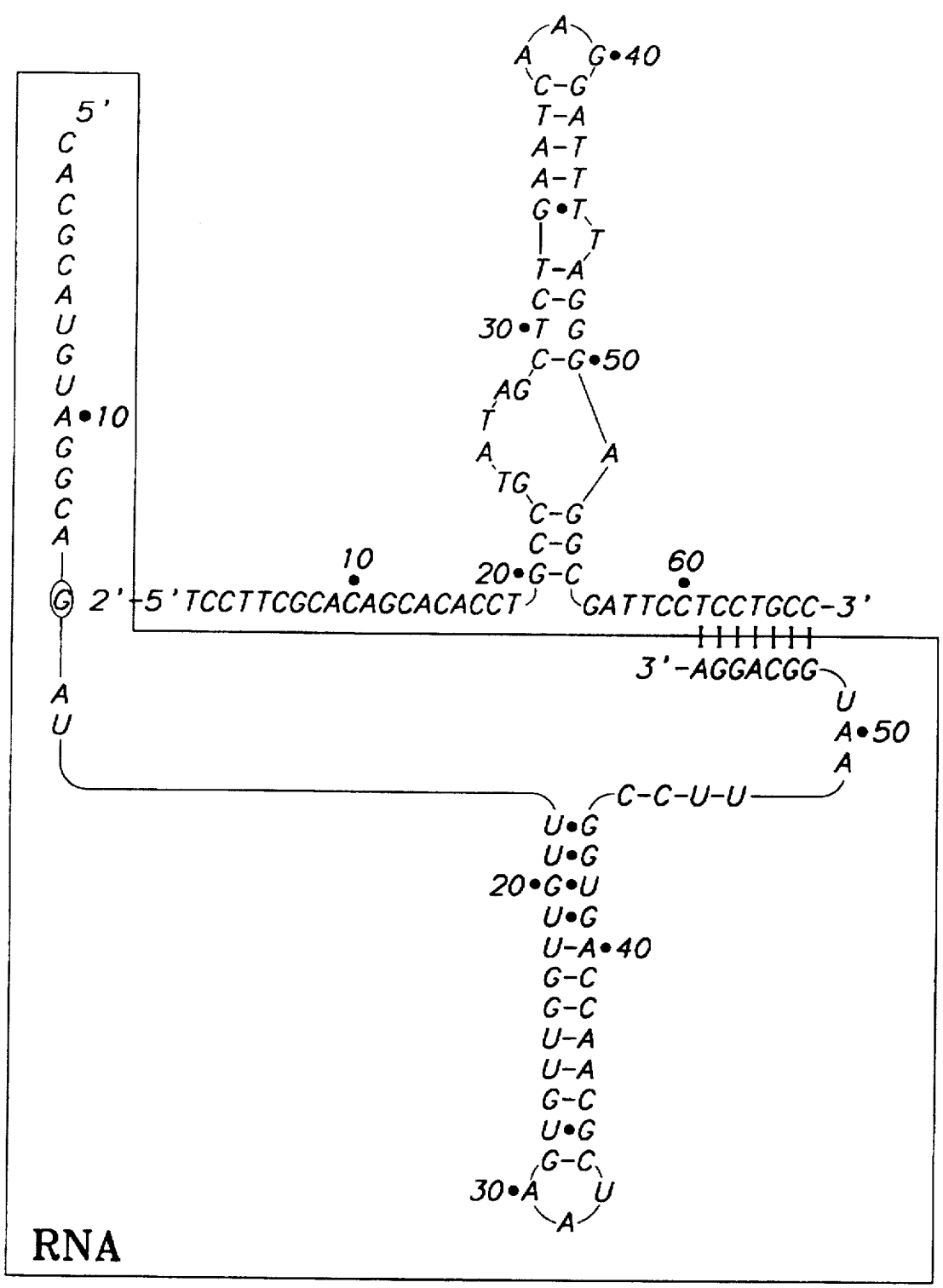
Figure 6C:
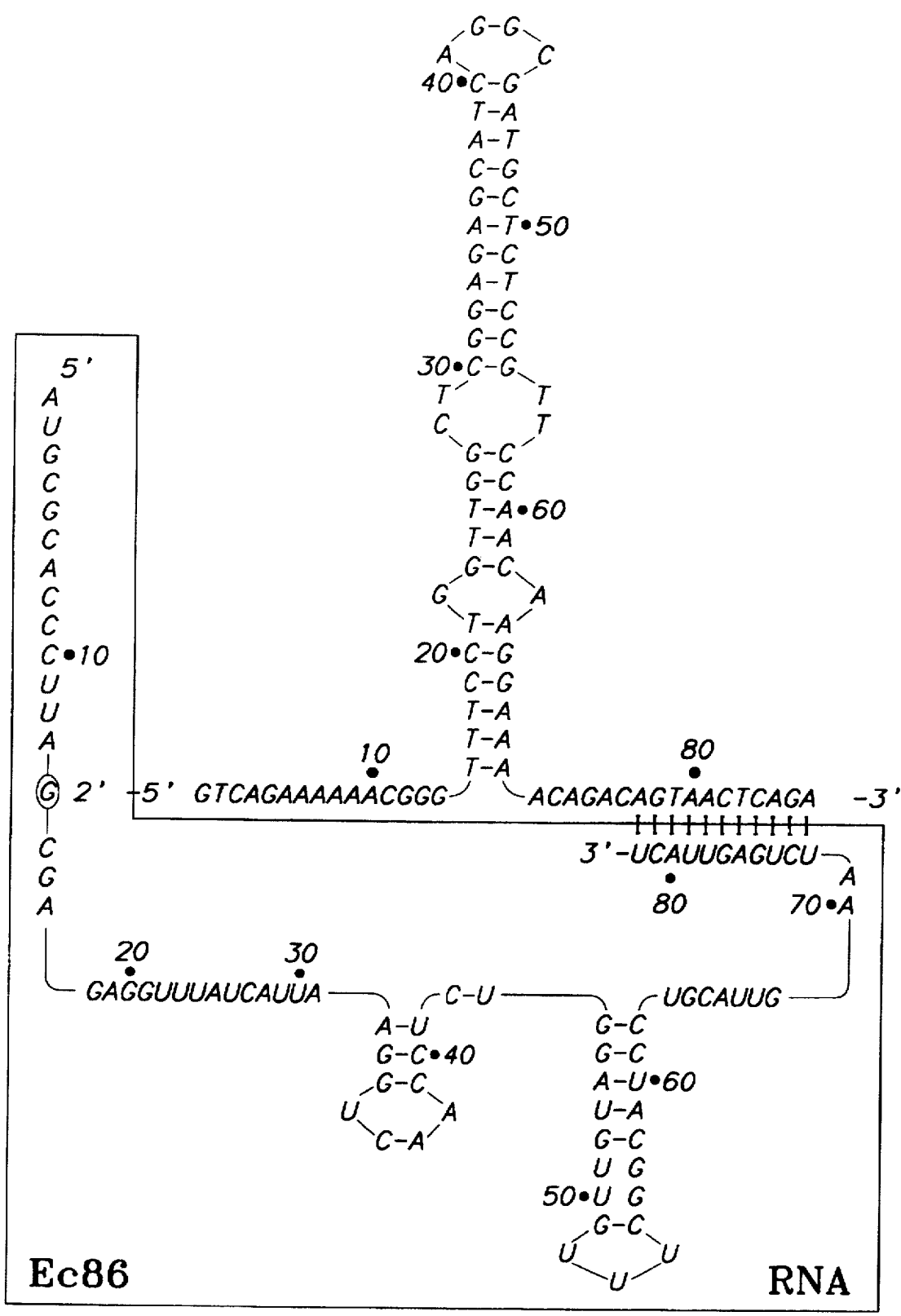
Figure 6D:
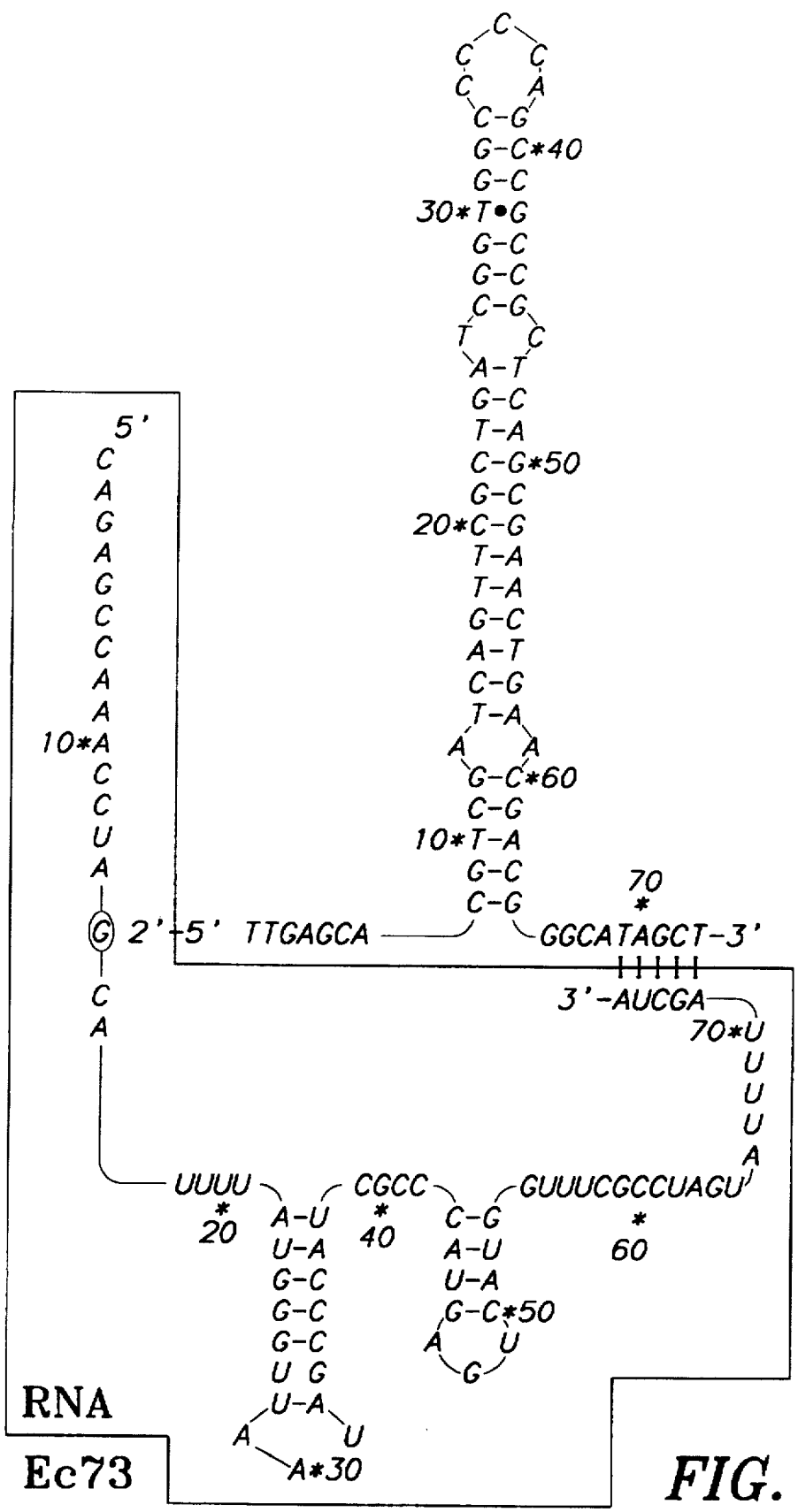
Figure 6E:
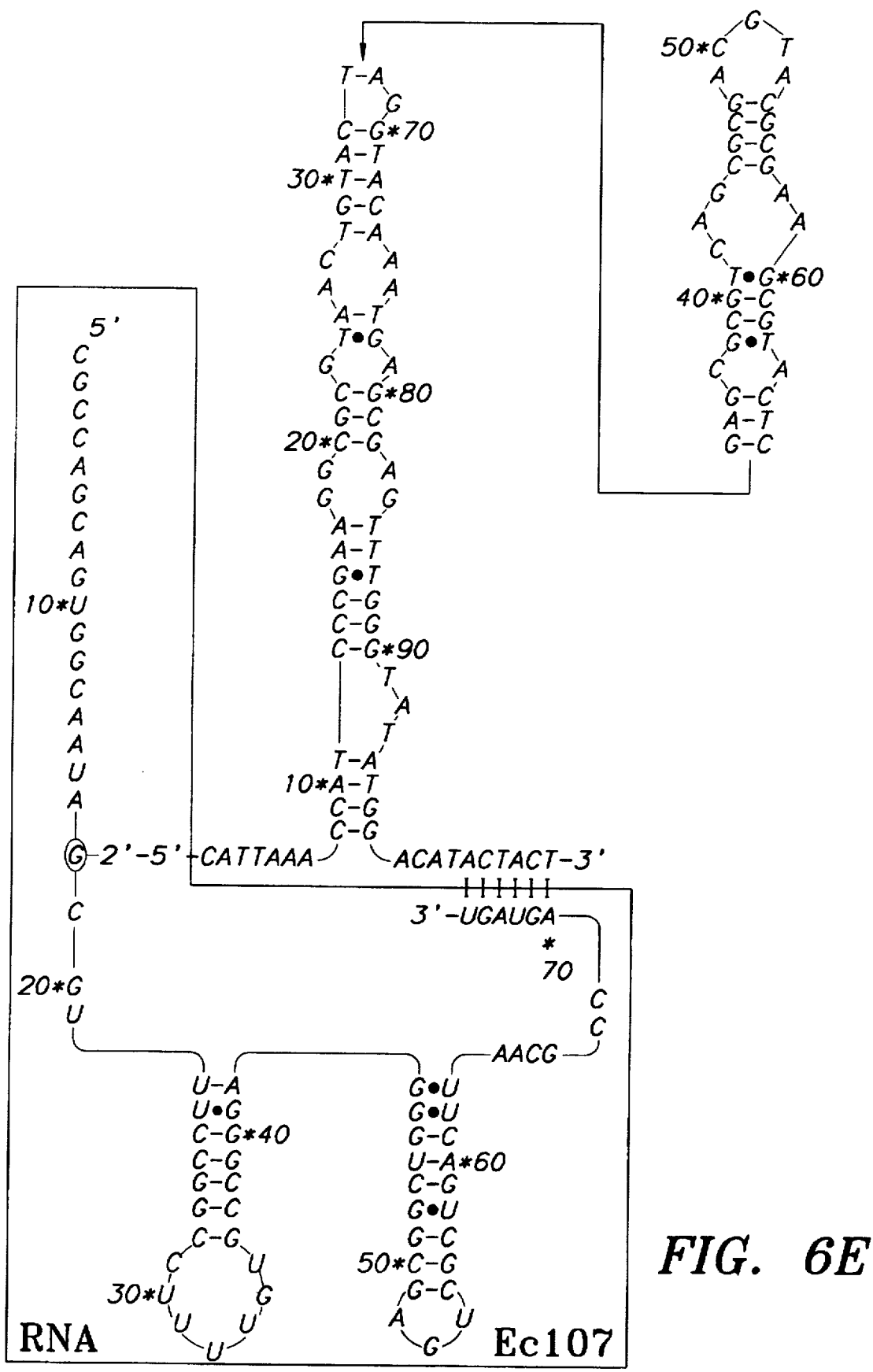
Figure 6F:
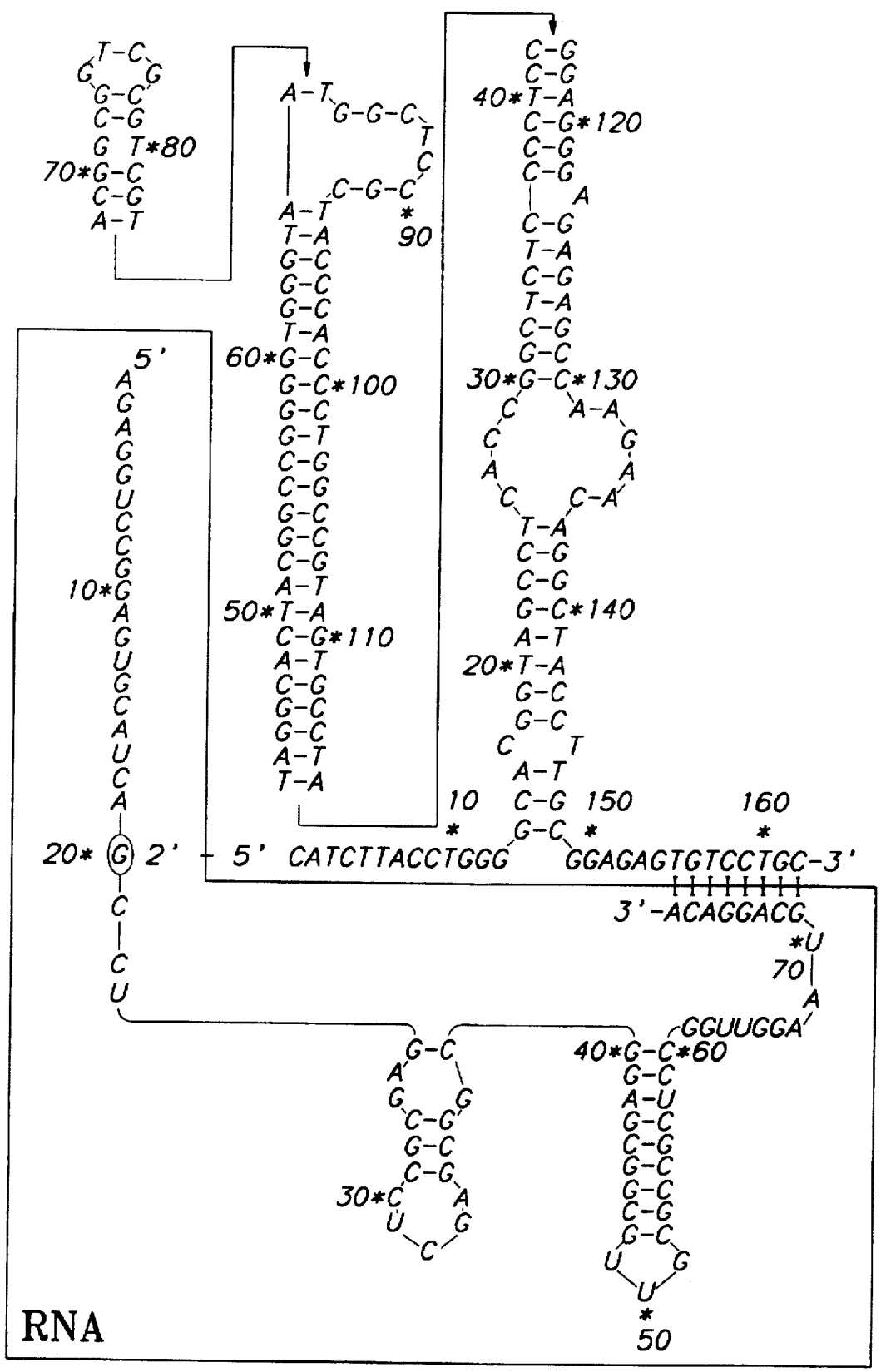
Figure 6G:
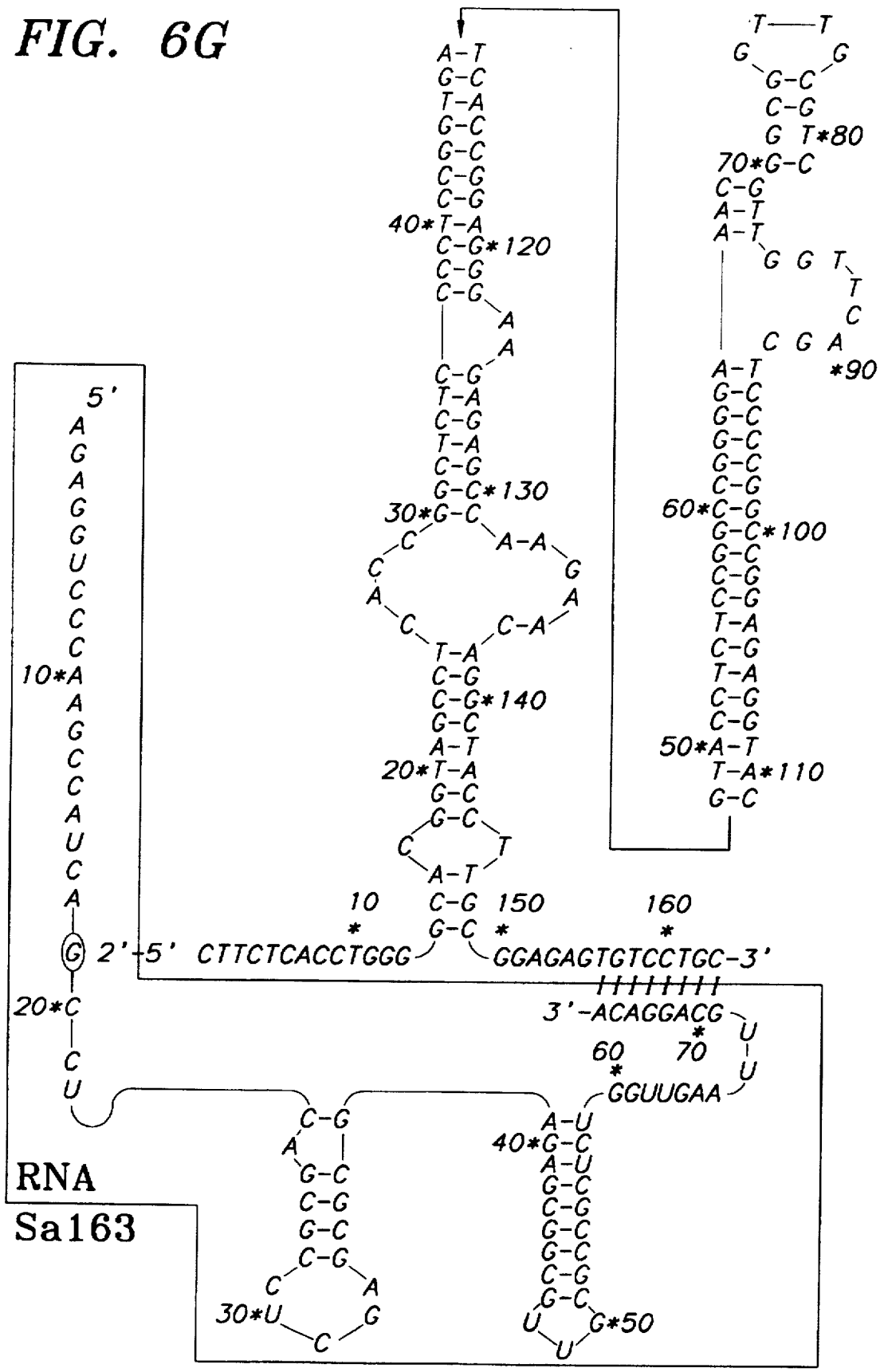
Figure 6H:
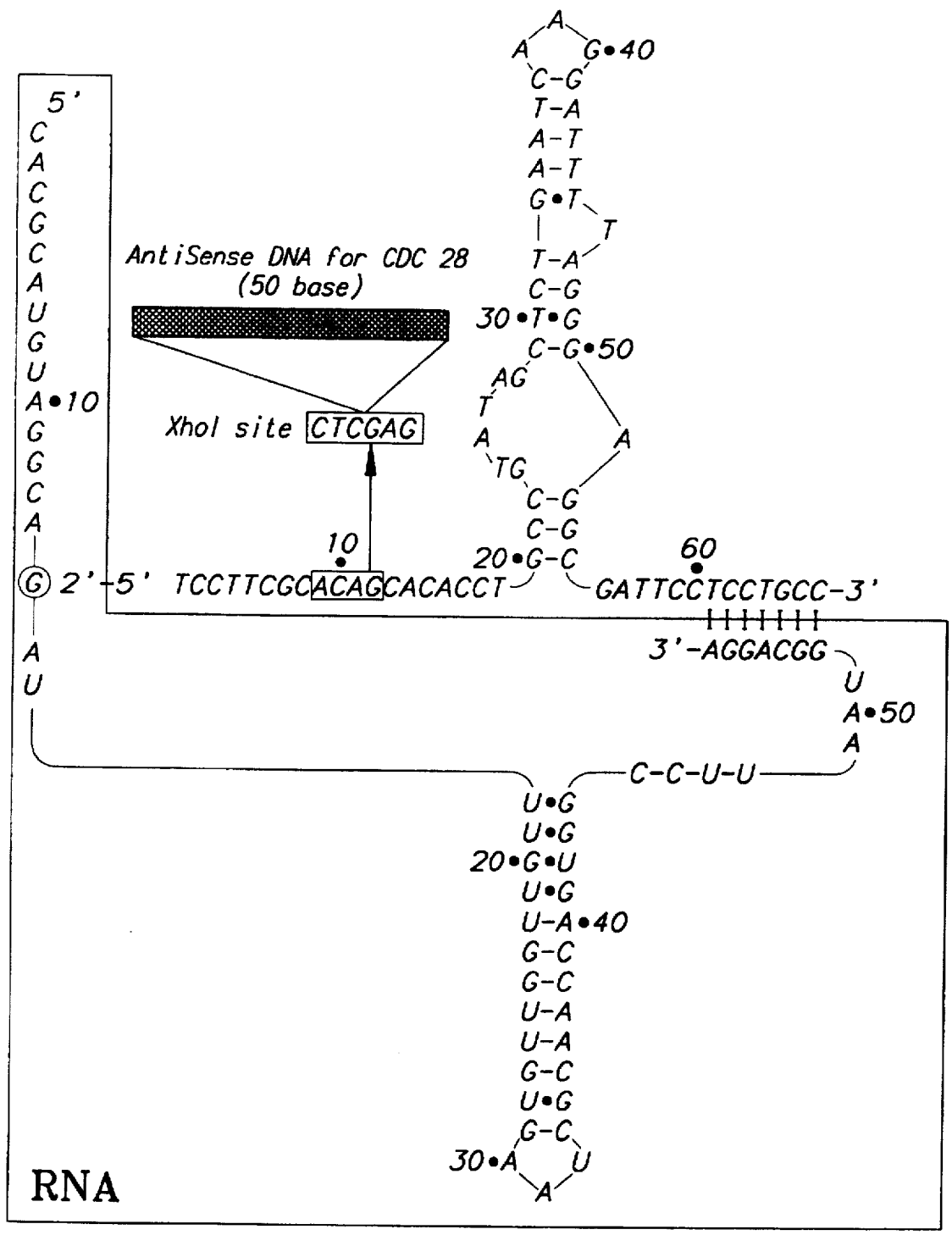
Figure 7:
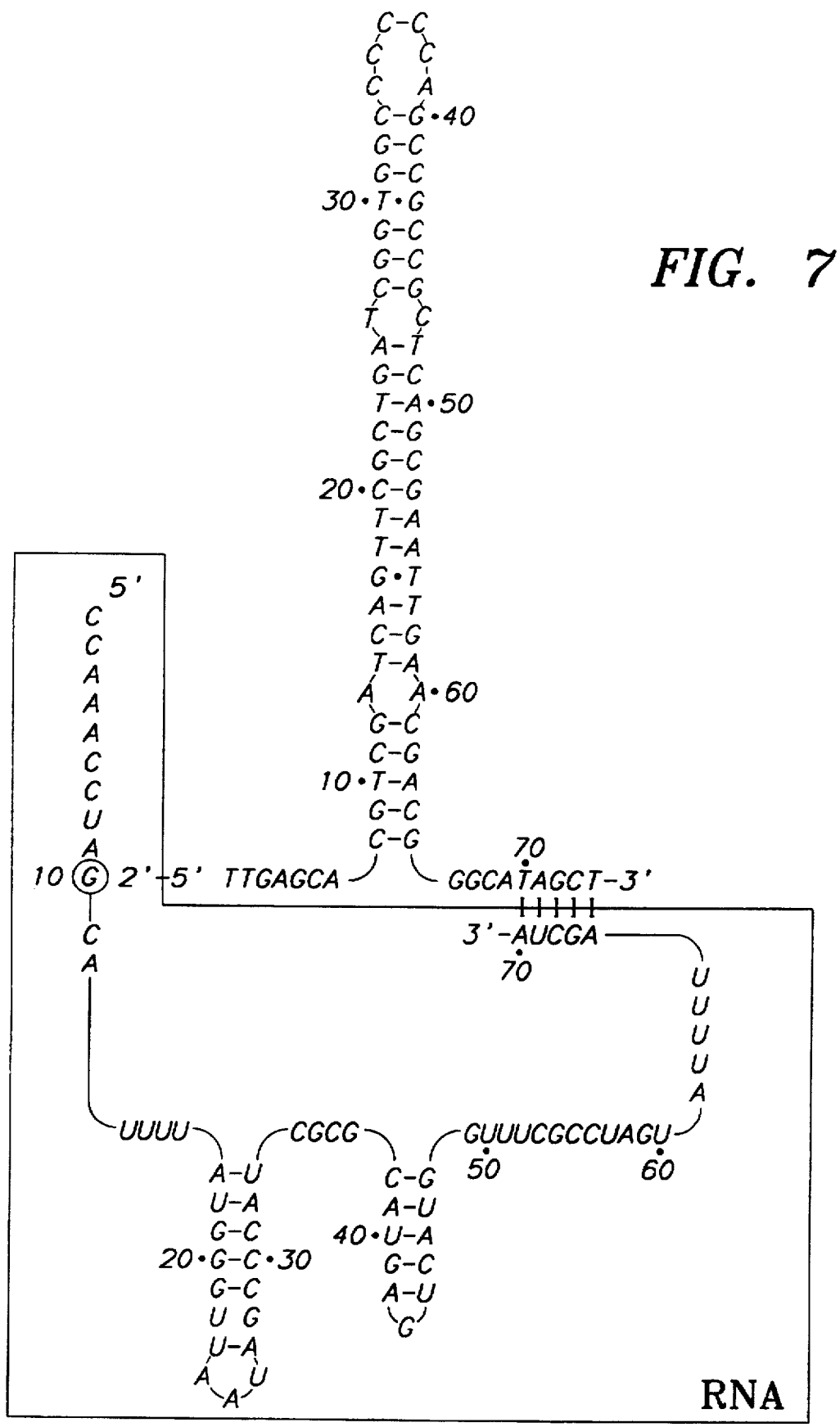
FIG. 7 shows another msDNA, Ec74(Seq ID Nos. 20 and 21).

Further, it should be noted that the ranges and nucleotide numbers given hereinabove do not include, but for species Ye117, FIG. 6(h), exogenous DNA or RNA fragments which can be inserted in the DNA and/or RNA portion of the msDNAs, or genes that will be found in final msDNAs as stem-loop structures.

Variations in the msr-msd (or in the msr or msd) region (or outside thereof) cause corresponding variations in the RNA transcript. Variations in the dNTPs (in a cell-free system) are reflected in the RNA portion of the molecule. All such variations of the basic msDNA are considered within the invention. For instance, when RNase A is not added to the reaction mixture in a cell-free synthesis of msDNAs, an msDNA is formed that contains a double-stranded segment in what is considered the RNA portion. All such and other variants of the generic msDNA molecule are considered within the scope of the invention.

msDNAs are encoded by a retroelement which has been designated as retrons. The retrons contain msr and msd genes, which code for the RNA and DNA strands, respectively, of msDNA. The two genes are positioned in opposite orientation. The retron comprises also an ORF encoding a polypeptide which has reverse transcriptase (RT) activity. The initiation codon of the ORF is situated as close as 19 base-pairs from the start of the msd gene for certain msDNAs, like in Ec86, but as distant as 77 base-pairs in other msDNAs like in Mx162. The ORF is situated upstream of the msd. but may also be situated downstream of the msd locus (i.e., downstream and upstream respectively of the msr locus). When the ORF is positioned in front or upstream of the msr region, increased yield of the msDNAs are obtainable in eucaryotic cells such as yeast.

The msDNAs are derived from a much longer precursor RNA (pre-msd RNA), which has been shown to form a very stable stem-and-loop structure. This stem-and-loop structure of pre-msdRNA serves as a primer for initiating msDNA synthesis, and as a template to form the branched RNA-linked msDNA. Transcription of msr-msd region of the retron, which forms the pre-msdRNA, initiates at or near the 5' end of msr, thus encompassing the upstream region of the msr and extends beyond msd to include the ORF. The 5' end sequence of the msr-msd transcript (base 1 to 13) forms a duplex with the 3' end sequence of the same transcript, this serving as a primer as well as a template for msDNA synthesis by RT. The promoter for the msr-msd region is upstream of msr, and transcription is from left to right, encompassing the entire region including the RT gene downstream of msr.

The RTs described herein are capable of forming a branched-linkage between the 2'-OH and any of the internal rG residues and the 5'-phosphate of the first deoxyribonucleotide triphosphate. This unique and quite unusual property of the RTs are further described herein below in conjunction with the synthesis of msDNAs.

The proposed mechanism of synthesis of the msDNAs comprises transcription of a long primary mRNA transcript beginning upstream from and including the msr region of the retron, extending to and including the msd region and including the ORF encoding the RT; folding of the primary mRNA transcript into stable stem-loop structures between and by means of two inverted repeat sequences, which folded mRNA transcript functions both as a primer and template for cDNA synthesis by RT; forming a branched linkage between the 2'-OH of an internal rG residue and of the 5' phosphate of the first deoxyribonucleotide of the cDNA strand and continuing cDNA synthesis by RT using the folded RNA as a template, with removal of the RNA template within the growing DNA/RNA duplex by means of RNase H processing and termination of msDNA synthesis. It is believed that activity of the RNase may be concomitant with that of the RT but this is not necessarily so.

The RT is capable by itself of synthesizing a cDNA (in this example, an msDNA molecule) utilizing the folded primary transcript, which transcript functions both as a primer and a template, by initiating synthesis with the formation of a unique 2',5'-linkage between the first deoxyribonucleotide residue of the cDNA molecule, and an internal rG residue of the particular msDNA molecule in the case of msDNA-Ec67, the 15th residue.

This activity is in contrast to known retroviral RTs, which are reported to initiate synthesis by formation of a 3',5'-linkage.

The primary transcript from the msr-msd region is folded to form a stem structure between the region immediately upstream of the branched rG residue and the region upstream of msd in such a way that the rG residue is placed at the end of the stem structure. In the mechanism described, msDNA synthesis is primed and cDNA synthesis commences from the 2'-OH of an rG internal residue using the bottom RNA strand as a template, this reaction being mediated solely by the RT encoded by the ORF of the primary transcript.

The synthesis of msDNAs, is initiated by an intramolecular priming event which starts at an internal guanosine residue (rG). The double-stranded nature of the 5' end of the folded primary transcript (due to its inverted repeat) functions as a priming site recognized by the RT.

In the situations where it is desired to use the RTs herein described to transcribe a non-self-priming template (or an mRNA that does not carry a poly(A) tail at the 3' end), it will be necessary to provide a suitable primer which will anneal to the mRNA in a conventional manner to provide the initiation site for the RT described herein to synthesize the single-strand cDNA along the template.

For background and protocols on synthesis of cDNA and reverse transcript, see *Molecular Cloning: A Laboratory Manual* ("Maniatis") pages 129–130 and 213–216 (incorporated herein by reference). If it is desired to separate any RNase activity when such is present, the protocols referred to in Maniatis in the Chapter on Synthesis of cDNA may be referred to (page 213). See also Marcus et al., *J. Virol.*, 14, 853 (1974) and other references cited at page 213. Other protocols are known in the art, such as including in the reverse transcription reaction mixture an inhibitor of RNase, such as vanadyl-ribonucleoside complexes or RNasin.

For further protocols, see *Molecular Cloning: A Laboratory Manual* ("Sambrook"), Vol 1, Units 5.34, 5.52–5.55 for RTs (RNA-dependentpolymerases); Units 7.79–7.83 for RNA primer extension, Vol. 2, Units 8.11–8.13, 8.60–8.63, 14.20–14.21 for first strand cDNA synthesis and 10.13 for synthesis of DNA probes with ssRNA template and 7.81 (and B.26) for suitable buffers (incorporated herein by reference).

RNA-directed DNA polymerases can be purified by methods known in the art. See Houts, G. E., Miyagi, M., Ellis, C., Brand, D., and Beard J. W. (1979), *J. Virol.* 29, 517. Also see *Current Protocols in Molecular Biology*, Vol. 1 ("Protocols"), Units 3.7.1–3.7.2 for description of RT isolation and purification (incorporated herein by reference). Roth et al., *J. Biol. Chem.*, 260, 9326–9335 (1985) and Verma, I. M., *The Enzymes*, Vol. 14A (P. D. Boyer, ed.), 87–104, Academic Press, New York, (1977); modified to the extent necessary for the RTs described herein. Also see, *BRL Catalogue*, page 17 (1985). Isolation & Purification of RTs described herein was according to the method described by Lampson et al., *Science*, 243, 1033–1038 (1989b). See also, Lampsonetal., *J. Biol. Chem.*, 265, 8490–8496 (1990).

There is provided hereinafter additional description of the various features identified above.

All RTs of the retrons show significant similarities in their amino acid sequences and the sequences found in retroviral RTs. They also contain the highly conserved polymerase consensus sequence YXDD found in all known RTs.

While the ORF is a common feature of the retron, the length of the ORF region can vary among the individual retrons for instance, from a minimum of 948 to a maximum of 1,758 nucleotides. The ORF region of MsDNA-Ec73 is 948 nucleotides in length; in Ec107, it is 957; in Ec86, it is 960; in Mx65, it is 1,281; in Mx162, it is 1,455 nucleotides in length and the ORF region of Ec67 is 586 nucleotides in length. The minimum number of nucleotides necessary is that which is effective to encode a polypeptide that has RT activity sufficient to contribute to the synthesis of the msDNA using the transcript as described herein.

Due to the extensive size differences of the RT ORFs, the domain structures are quite diverse. All but one RT (from msDNA-Ec67 (RT-Ec67)) do not contain a RNase H domain. All RTs from myxobacteria contain an extra amino terminal domain of 139 to 170 residues, while RTs from *E. coli* (except for RT-Ec67) have only an RT domain and consist of 316 to 320 residues. The amino acid sequence of RT-Sa163 consists of 480 residues which shown 78% identity with the sequence of RT-Mx162.

It is noteworthy in that certain of the RTs described herein can use heterologous msDNAs as template primers to extend the synthesis of msDNA in vitro. For instance, purified Ec67-RT can use heterologous msDNAs, Ec86 and Mx162 for such purpose.

As has been noted above, the msr-msd region and the RT gene can be expressed under independent promoters to produce msDNAs. However, the msr-msd region for the production of msDNA-Ec67 can only be complemented by the RT-Ec67, but not by the RT-Ec73 gene or vice versa. This specificity may be due to the priming reaction for each msDNA. With respect to promoter(s), msr-msd and the RT may be driven by a single promoter upstream of the msr-msd region or the RT gene may be driven by a separate promoter, for instance the yeast lpp-lac promoter. The promoter may be an endogenous or a foreign promoter like the GAL10 promoter.

There will be described hereinafter various methods of synthesizing the msDNAs. A number of methods of making the msDNAs of the invention are described in our earlier patent applications. For example, the msDNAs of the invention have been synthesized in vivo in suitable prokaryotes or eukaryotes. The msDNAs can also be synthesized by chemical methods, in cell permeabilized or in cell-free systems.

A cell-free method of making msDNAs in vitro comprises permeabilizing the membrane of a suitable prokaryotic cell by treating with a suitable cell permeabilizing agent, incubating said permeabilized cells in a reaction mixture with suitable substrates for msDNA synthesis and isolating and purifying the synthesized msDNA of the invention. Detailed description is found in pending application Ser. No. 07/315, 427, referred to above.

The msDNAs of the invention may be synthesized in vivo in suitable host cells. The msDNAs may be synthesized in prokaryotic cells. Likewise, eukaryotic cells may also be utilized to synthesize the msDNAs of the invention. See U.S. patent application Ser. No. 07/753,110. The method of making the msDNAs of the invention in vivo comprises culturing a suitable cell containing a rDNA construct encoding a prokaryotic msDNA synthesizing system, which includes the ORF region. See U.S. patent application Ser. No. 07/517,946). The synthesizing systems include retrons which encode the msDNAs of the invention. See U.S. patent application Ser. No. 07/518,749. The cells were transformed with suitable plasmids constructed with the retrons. msDNAs typical of the invention, as shown in FIGS. 1. 2 and 3. After synthesis they are isolated and purified.

Suitable prokaryotic cells for the in vivo expression of the msDNAs of the invention are *M. xanthus* and *E. coli*. Suitable eukaryotic cells are yeasts, e.g., *Saccharomyces cerevisiae*. Any suitable prokaryotic or eukaryotic cells capable of expressing the msDNAs of the invention can be used.

There will be described hereinafter, several interesting utilities of the RTs and msDNAs. The RTs described herein (and in earlier above-referred to patent applications) are believed to be valuable in assays for screening different molecules for their effect to inhibit or block the activity of the RTs both in vivo and in vitro.

Since the msDNA production in vivo can be monitored either biochemically or genetically, it can be used for screening drugs which block the msDNA synthesis. If such drugs are found, they may block the msDNA synthesis at the unique 2'-OH priming reaction (the formation of a 2',5'-phosphodiester linkage) or the extension of msDNA synthesis (or cDNA synthesis).

An in vitro assay is thus provided which comprises a suitable template, RNA or DNAs (or a molecule which contains such a template), an RT of the invention and a molecule to be screened (and other conventional components) to allow the RT activity to manifest itself. The greater the inhibitory or blocking effect of the screened molecule(s) on the RT activity, the more likely the molecule will be as a useful candidate for biological and medical applications where it is sought to inhibit a disease due to a retrovirus such as HIV, HTLV-I and others.

Since the synthesis of msDNAs are RT-dependent, the molecules to be screened for effect on RT activity can be tested in the vitro synthesis of the msDNAs. The extent to which that synthesis is inhibited determines the effectiveness of the molecule(s).

Another suitable molecule that can be used as a template, are single-stranded DNA cloning vehicles such as the M13 cloning vectors (mp 8). See *Molecular Cloning: A laboratory Manual* ("Sambrookt"). Vol. 1. Units 4.33–4.38 for cloning foreign DNA into bacteriophage M13 vectors and Unit 1.20. Bluescript M13$^+$ and M-13$^-$ (incorporated herein by reference).

Since the msDNA is produced in several hundred copies per retron, the msDNA can be used for gene amplification. This can be performed by classic protocols by splicing into the stem portion of a stem-and-loop region of the msDNA, a double-stranded DNA containing a gene or by replacing a portion of the stem-and-loop region by a double-stranded DNA containing a desired gene. For instance, in the synthetic msDNAs shown in FIGS. 3*a* and 3*b*, the stem-and-loop region of the msDNA can be cut out by an appropriate restriction enzyme from the retron containing plasmid DNA having restriction site XhoI and SacII. A DNA fragment is then ligated into the site which contains two copies of a gene of interest either in head to head or tail in tail orientation. When this region is copied as a single-stranded DNA into the msDNA, a stem-and-loop structure is formed because of the palindromic orientation of the two copies of the genes. Thus, the gene of interest is reconstructed in the stem structure. By this method of gene amplification, a large number of genes can be produced. When the msDNA structure is not foreign to *E. coli*, this microorganism is particularly well suited as a vehicle for gene multiplication.

In another application, the msDNAs of the invention are used to produce stable RNAs.

The msDNAs of the invention are useful in the production of polypeptides and in the production of antisense molecules. Polypeptides will be produced from DNA fragments inserted in the retron such that the sense strand is transcribed.

The msDNAs of the invention are useful as a vector for the production of recombinant antisense single-stranded DNAs. Antisense molecules will be produced from DNA fragments inserted in the retron in an orientation such that the primary transcript contains an antisense strand. Such msDNAs are especially useful because of their stability in contrast to antisense molecules known to date which are comparatively unstable. Selected DNA fragment can be inserted into the msr or the msd region of the retron. The primary transcript in turn will contain an RNA sequence complementary to the inserted DNA fragment in addition to the msr, msd regions and the ORF for the RT. The DNA fragment containing the gene of interest can be inserted in either orientation such that the primary transcript will contain either the sense strand and function as an mRNA, i.e., produce a polypeptide, or the antisense molecule strand, in which case the primary transcript will anneal to the target gene mRNA and inhibit its expression. The msDNA produced therefrom operates as an antisense against the mRNA produced in vivo from the target gene and thus can be used to regulate the expression of the gene in vitro. The DNA fragment can be inserted into either the msr or the msd region of the retron. The target gene will then be expressed in the RNA or DNA portion of the msDNA, respectively. The insertion into the msr or msd region can be performed in any suitable restriction site as is known in this field of technology.

The expression of an antisense molecule as an msDNA is highly advantageous. Antisense molecules produced to date are known to be inherently unstable and rapidly degraded. In contrast, the msDNAs carrying the antisense fragment exhibit remarkable stability. Such msDNAs contain in either the RNA or the DNA portion an antisense strand that is complementary to and capable of binding or hybridizing to and inhibiting the translation of the mRNA of the genetic material or target gene. Upon binding or hybridizing with the mRNA, the translation of the mRNA is prevented with the result that the product such as the target protein coded by the mRNA is not produced. Thus, the msDNAs provide useful systems for regulating the expression of any gene and contribute to overcoming the problem of lack of stability associated with antisense molecules of the prior art.

Antisense technology has been widely used for regulating gene expression. Single-stranded RNA or DNA complementary to a target mRNA can inhibit the translation of the mRNA. Antisense RNA is produced in vivo, while antisense DNA is chemically synthesized as an oligonucleotide, which is extracellularly added to the cells. To maintain the effect of antisense DNA, a synthetic oligonucleotide has to be constantly added to the system. An advantage of antisense DNA over antisense RNA is that the target mRNA hybridized with the antisense DNA can be specifically digested by ribonuclease H.

For an illustration of an msDNA carrying an antisense fragment, reference is made to pending patent application Ser. No. 07/753,110. Any of the msDNAs can be used for that purpose.

When it is desired to insert a DNA sequence in an msDNA for encoding a protein (polypeptide) eg., two copies of a gene will be inserted in tandem and in opposite orientation with respect to another at a selected restriction site into the msd sequence of an msDNA of choice, such as YEp521-M4.

The msDNAs may be useful in HIV therapy as follows. Healthy lymphocytes are taken from a patient and stored. When needed by the patient, the msDNAs would be proliferated; a DNA construct is inserted into the msDNA which would produce an antisense against one of the HIV essential proteins, then transfuse these lymphocytes back into the patient. Thus, a growing population of lymphocytes develop which will be resistant to HIV.

For literature and other references relating to antisense RNA and its application in gene regulation, see for instance: Hirashima et al., *Proc. Natl. Acad. Sci. USA*, 83, 7726–7730 (October 1986) and Inouye, *Gene*, 72, 25–34 (1988); and European Patent Application A2 0 140 308, published May 8, 1985, entitled "Regulation of gene expression by employing translational inhibition utilizing mRNA interfering complementary RNA", based on U.S. patent applications Ser. No. 543,528 filed Oct. 20, 1983 and Ser. No. 585,282 filed Mar. 1, 1984, which are incorporated herein by reference.

For an up to date report on antisense, see *Antisense Research and Development*, 1, 207–217 (1991), Hawkins and Krieg, Editors; Mary Ann Liebert, Inc., Publishers. See "Meeting Report: Gene Regulation by Antisense RNA and DNA", for a listing of patents in that field, see "A Listing of Antisense Patents, 1971–1991" therein. The msDNAs of the invention are useful in numerous applications described therein.

A fascinating utility considered is the role of the msDNAs of the invention in the formation of triple-helix DNA, or triplex DNA with a specific duplex on the chromosome. A recent report in *Science*, 252, 1374–1375 (Jun. 27, 1991), "Triplex DNA Finally Comes of Age", highlights the timeliness of the present invention. Triplex DNA can be formed by binding a third strand to specific recognized sites on chromosomal DNA. Synthetic strands of sizes preferably containing the full complement of bases (such as 11–15 and higher), are discussed. The msDNAs of the invention appear to be excellent candidates for such applications. The msDNAs provide single-stranded DNAs necessary for triplex formation. The resulting triplex DNA is expected to have increased stability and usefulness. New therapies based on the triple-helix formation, including the AIDS therapy and selective gene inhibition and others are proposed in the Report.

Other applications can be envisioned by one skilled in the art.

A third embodiment of the invention relates to a cell-free synthesis of a typical msDNA. The method comprises reacting a total RNA preparation containing the msr-msd region and a purified RT (such as Ec67-RT) under conditions suitable for the reaction.

Using this cell-free system, the priming reaction, during initiation of DNA synthesis, was demonstrated to be a specific template directed event. Only dTTP was incorporated into a 132-base precursor RNA yielding a 133-base compound. This specific dT addition could be altered to dA or dC by simply substituting the 118th A residue of the putative msr-msd transcript with a T or G residue. The priming reaction was blocked when A was substituted for G at the 15th residue of the precursor RNA transcript which corresponds to the branched rG residue in msDNA. DNA chain elongation could be terminated by adding ddNTP in the cell-free system, forming a sequence ladder. The DNA sequence determined from this ladder completely agreed with the msDNA sequence. A part of the fully extended cell-free product contained a 13-base RNA strand resistant to RNase A, which was consistent with the previously proposed model. In this model the 5'-end sequence of the msr-msd transcript (base 1 to 13) forms a duplex with the 3'-end sequence of the same transcript, thus serving as a primer as well as a template for msDNA synthesis by RT.

As described hereinabove, the msDNA synthesis is primed from the 2'-OH residue of the rG residue using the bottom RNA strand as a template. The first base or the 5'-end of msDNA is determined by the base at position 118 in FIG. 1C. Thus, the synthesis of msDNA-Ec67 starts from a dT residue, complementary to the rA residue at position 118. See FIG. 1C.

In other msDNAs, the internal G residue occurs at different locations as described above. Thus, in the synthesis of other msDNAs the synthesis starts at the base in the DNA which is complementary to the first base in the RNA strand.

Figure 2:
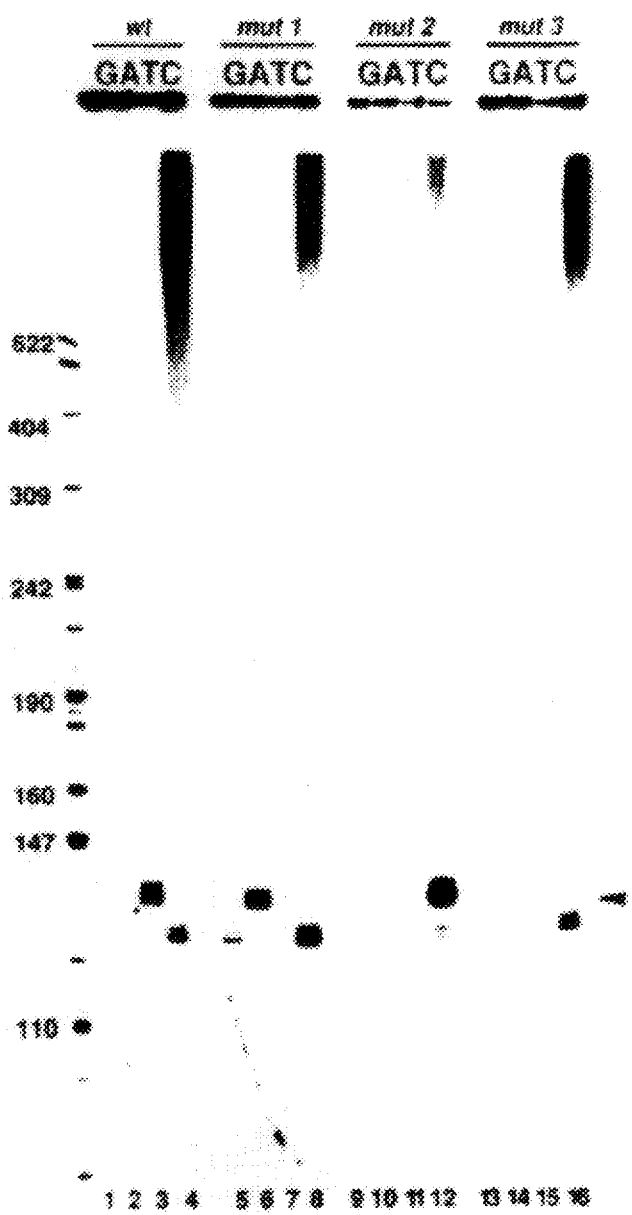
FIG. 2 shows specificity of the priming reaction of msDNA-Ec67 synthesis in vitro. The reaction for the first base addition was carried out as described in Experimental Procedures; the reaction mixture contains an RNA fraction from a 1-ml culture and 5 µCi of each [α-$^{32}$P]dNTP in separate reactions in 10 µl of RT buffer. The reaction was started by adding 2 µl of the partially purified RT and the mixture was incubated at 37° C. for 30 minutes. Lanes 1 to 4, the reaction was carried out with the RNA fraction from CL83 cells harboring p67-BHO.6 (wild-type); lanes 5 to 8 from cells harboring p67-mut-1 for the A to T mutation at position 118 in FIG. 1C (mutation 1); lanes 9 to 12, from cells harboring p67-mut-2 for the A to G mutation at position 118 in FIG. 1C (mutation 2); and lanes 13 to 16, from cells harboring p67-mut-3 for the G to A mutation at position 15 in FIG. 1C. [α-$^{32}$P]dNTP used for each lane is indicated on the top of each lane. The MspI digest of pBR322 labeled with the Klenow fragment with [α-$^{32}$P]dCTP was applied to the extreme left-hand lane as molecular weight markers. Numbers indicate sizes of fragment in bases. An arrowhead indicates the position of the precursor RNA molecule specifically labeled with dNTP for each RNA preparation.

There is established first a cell-free system for the synthesis of msDNA-Ec67 using partially purified RT-Ec67 and the RNA fraction prepared from cells harboring p67-BHO.6. This plasmid contained the msr-msd region and a truncated RT gene from retron-Ec67 as described in the Examples. As shown in FIG. 2, $[\alpha\text{-}^{32}P]dTTP$ (lane 3) was specifically incorporated into a product migrating at the position of 133 nucleotides in size. Neither |α-$^{32}$P|dGTP (lane 1) nor |α-$^{32}$P|dATP (lane 2) was incorporated in the cell-free system. In the case of |α-$^{32}$P|dCTP (lane 4), two minor bands appeared at positions shorter by 4- to 5-bases than the major product labeled with |α-$^{32}$P|dTTP (lane 3). As discussed later, these products were labeled even in the absence of the branched rG residue (lane 16, FIG. 2), indicating that these were not associated with msDNA synthesis. When RT was omitted from the reaction mixture, no labeled bands were detected with |α-$^{32}$P|dTTP.

Figure 1B:
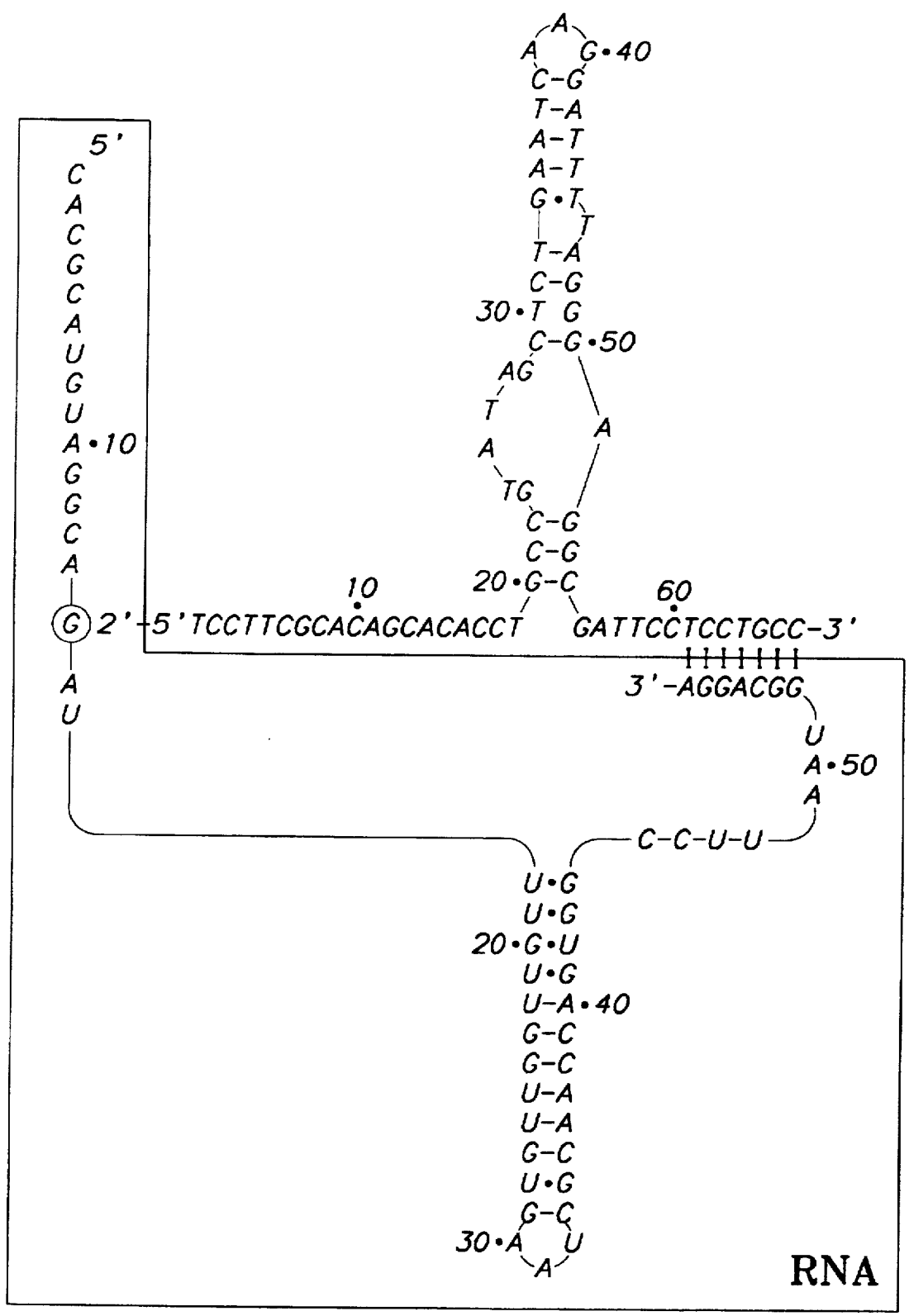
Figure 1C:
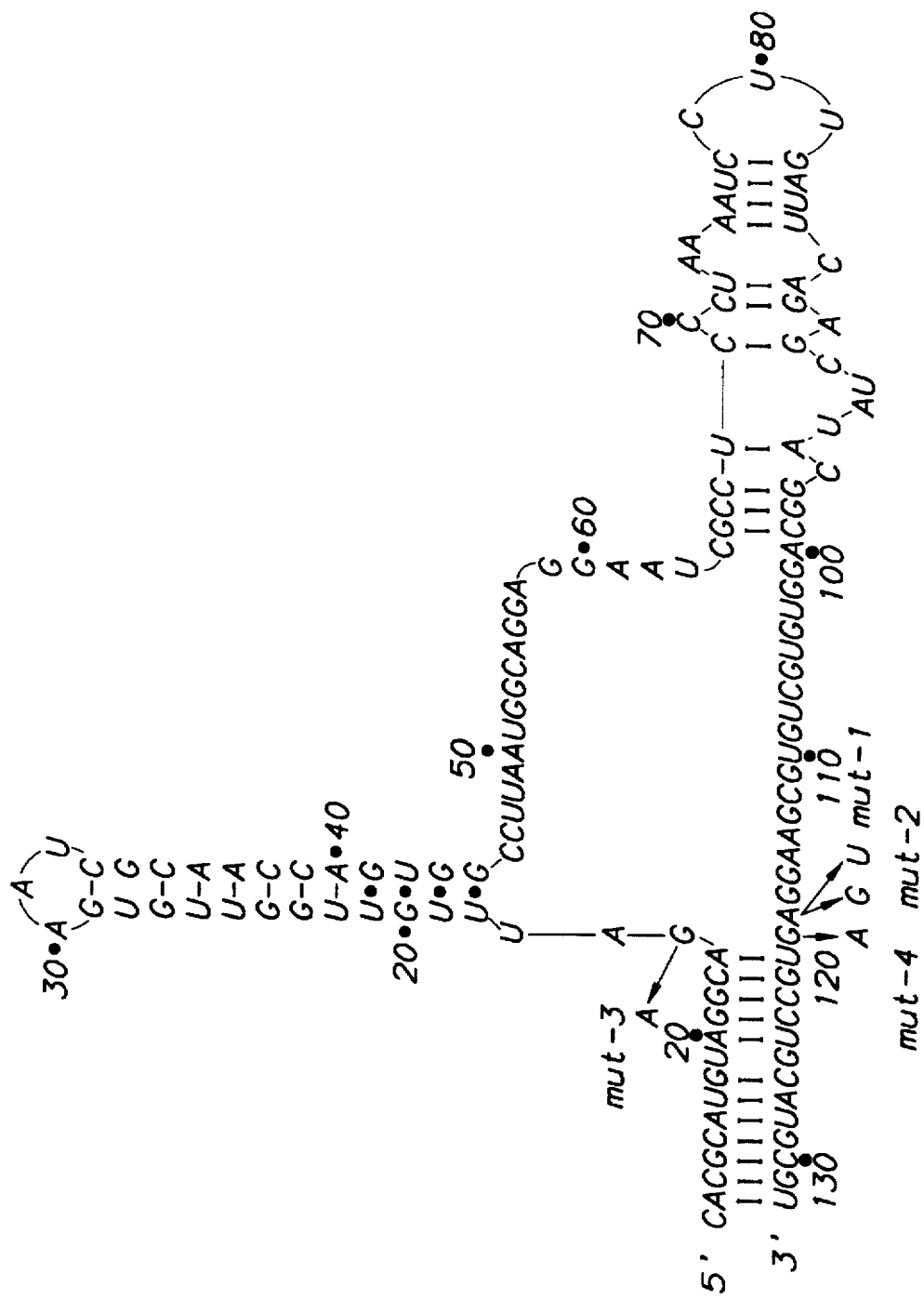
Figure 3:
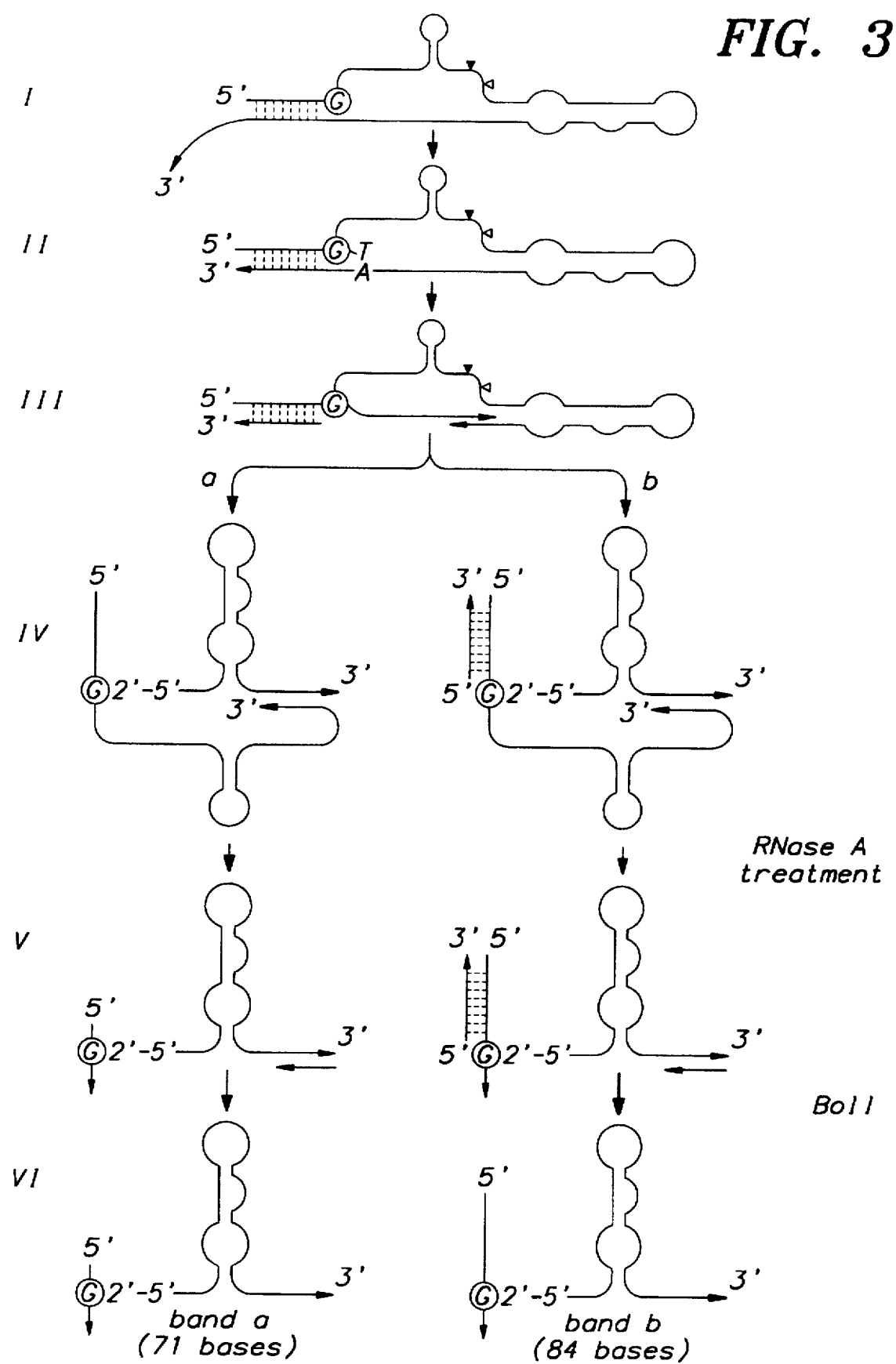
FIG. 3 shows schematic diagram of the production of bands a and b. Thin and thick lines represent RNA and DNA, respectively, and the arrowheads indicate the 3'-end. Open and filled triangles indicate the 3'-ends of the RNA and DNA strands, in msDNA, respectively. Broken lines indicate base pairings in the double-stranded RNA structure at the 5'-end of msdRNA. Structure I is first formed from the primary transcript from retron-Ec67. The unhybridized 3'-end is probably removed in the cells; the resulting structure is identical to that shown in FIG. 1C. When dTTP is added with RT-Ec67 in the cell-free reaction mixture, a dT is linked to the 2'-OH group of an internal rG residue (circled in the Figure) by a 2',5'-phosphodiester linkage (structure II). When the other three dNTPs are added, the DNA strand is elongated along the RNA template. As the DNA strand is extended, the RNA template is concomitantly removed (structure III). The DNA synthesis is terminated at the position indicated by a solid triangle, leaving a 7-base DNA-RNA hybrid at their 3'-ends, yielding structure IVa or IVb. RNase A treatment of structure IV results in structure V. When structure V is incubated in a boiling water bath, structure VI is formed. Structures VIa and VIb correspond to bands a and b in FIG. 2, respectively.

The size of the product labeled with dTTP agrees well with that of the structure proposed in FIG. 1C; the folded RNA precursor consists of 132-bases and the addition of a dT residue to the RNA molecule yields an oligonucleotide consisting of 133-bases (see also structure III in FIG. 3).

Two mutations were then constructed; in the first mutation the rA residue at position 118 of the precursor RNA molecule (FIG. 1C) was substituted with an U residue (mut-1) and in the second mutation with a rG (mut-2). When the mut-1 RNA preparation was used for the priming reaction, |α-$^{32}$P|DATP was specifically incorporated into the major product (lane 6, FIG. 2) migrating at the same position as the product labeled with |α-$^{32}$P|dTTP using the wild-type RNA fraction (lane 3). Similarly |α-$^{32}$P |dCTP was specifically incorporated with the mut-2 RNA preparation (lane 12). It should be noted that the A to G substitution in mut-2 resulted in three consecutive rG residues on the template strand of the RNA molecule (from base 116 to base 118; see FIG. 1C). Therefore, one to three dC residues are expected to be added to the precursor molecule. Indeed, the band labeled with |α-$^{32}$P|dCTP in lane 12, FIG. 2 was much broader towards higher molecular weights than the wild-type product (lane 3) and the mut-1 product (lane 6). Thus, it appears that the nature of the residue at position 118 (in the case of that msDNA) is not critical.

Previously it was demonstrated that the branched rG residue is essential since the substitution of the G residue with an A residue completely blocked the synthesis of msDNA-Mx162 in vivo. Similarly, in the present cell-free system, the G to A substitution (mut-3 at position 15 in FIG. 1C) completely abolished the specific |α-$^{32}$P|dTTP incorporation into the precursor RNA (compare lane 15 with lane 3 in FIG. 2). Doublet bands are still produced with |α-$^{32}$P| dCTP even with the mut-3 RNA preparation (lane 15), indicating that these bands are not associated with msDNA synthesis.

In all known msDNAs from both myxobacteria and E. coli, the base directly opposite to the branched G residue in the folded RNA precursor is always an rG residue without exception (residue 119 in FIG. 1C). When this rG residue at position 119 was changed to A (mut-4), the specific dT incorporation was still observed but the incorporation was substantially reduced (approximately to 5% of the wild-type incorporation). This indicates that this rG residue on the template strand plays an important role in the priming reaction. When the products from the priming reaction in FIG. 2 were digested with RNase A, all yielded products of small molecular weights migrating almost at the front of gel electrophoresis.

Thus, the studies described above clearly demonstrate that the first base was added to the precursor RNA molecule in a specific manner such that the first base is complementary to the base positioned at the A residue in structure II in FIG. 3. Furthermore, the addition of the first base is absolutely dependent upon the RT preparation added in the reaction and also upon the rG residue (circled in FIG. 3) at the end of the a1-a2 stem. The T residue (complementary to the rA residue at position 118) linked to the branched rG residue then serves as a primer to further extend the DNA chain along the RNA template. As the DNA strand is extended, the RNA template is concomitantly removed as shown in structure III so that the total number of bases of structure III is almost identical to that of structure II.

In other DNAs, likewise the base residue complementary to the base residue is a position equivalent to 118 is the base from which the DNA chain extends along the RNA template.

Figures 4, 5:
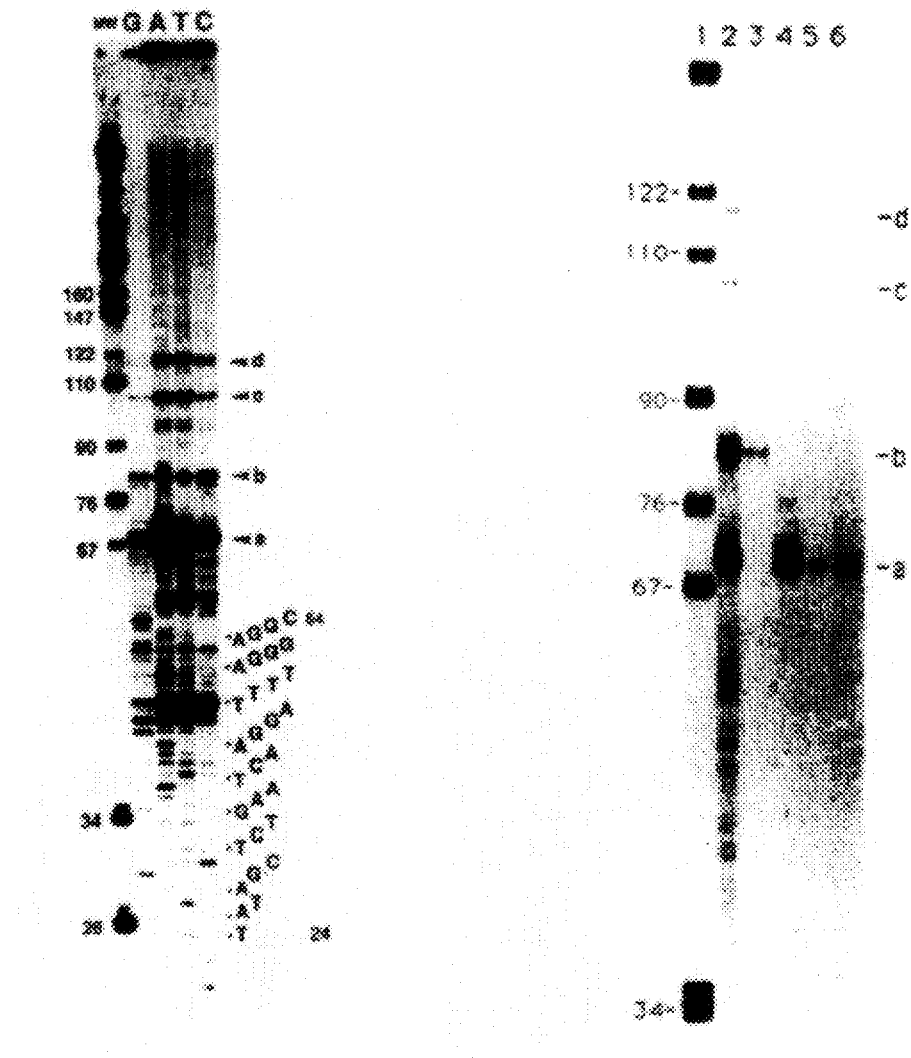
FIG. 4 shows chain termination reaction during msDNA synthesis in the cell-free system. The extension reaction for msDNA synthesis was carried out in the presence of dideoxy NTP as described in *Experimental Procedures*. Individual chain termination reaction mixtures containing either ddGTP, ddATP, ddTTP and ddCTP were applied to lanes G, A, T and C, respectively. The resulting ladder was read at the right-hand side which corresponds to the DNA sequence of msDNA-Ec67 from base 24 to 54 (see FIG. 1C; Lampson et al., 1989b). The same molecular weight markers as in FIG. 2 were applied to the extreme left-hand lane, and the sizes in the bases are indicated at the left-hand side. Four major products are indicated by arrows with a, b, c and d as schematically drawn in FIG. 3.
FIG. 5 shows ribonuclease treatment of the band b and d products. The products after the full extension reaction in the cell-free system (without ddNTP) were applied to a DNA sequencing gel (lane 2). Band b (lane 3) and band a (lane 4) were isolated from preparative gel electrophoresis, and digested with RNase A (lanes 5 and 6, respectively). The molecular weight markers (lane 1) are the same as in FIG. 2.

In order to confirm this model, the chain elongation reaction was carried out using the same cell-free system as used for the first base addition in FIG. 2; in addition to |α-$^{32}$P|dTTP, three other dNTPs as well as dideoxynucleotides (ddNTPs) were added for separate chain-termination reaction (Sanger et al., 1977). After the chain-elongation reaction, the products were treated with RNase A to remove single-stranded RNA attached to them. As can be seen in FIG. 4, a ladder is formed, clearly indicating that the DNA chain was elongated using a specific template sequence. The sequence determined from the ladder is identical with the DNA sequence from base 24 to base 54 of msDNA-Ec67 (FIG. 1B). Although some termination of msDNA synthesis occurred at around positions 42 to 44, most of the reaction terminated at around position 69 forming a strong band in all lanes at position (a). This product is most likely the fully extended msDNA-Ec67 (67-base single-stranded DNA) that is linked to a 4-base RNA, AGAU resulting from RNase treatment (structure IVa in FIG. 3). The DNA strand is considered to be branched out from the 2'-OH group of the G residue of the tetranucleotide. Every band in the sequencing ladder migrated at a position longer by 2-bases than what was expected from the size of the DNA strand. This was probably caused by the extra 4-base RNA attached at the 5'-end of the DNA strand. The 2-base discrepancy in the mobility in the gel is likely to be due to the branched RNA structure.

RNA Structure at the 5'-End—The structure of msDNA-Ec67 produced in vivo has been determined as shown in FIG. 1B (Lampson et al., 1989b), which corresponds to structure IVa in FIG. 3. On the basis of the proposed model shown in FIG. 3, structure IVb may also be produced, in which the 5'-end arm of the msdRNA (upstream of the branched rG residue and the sequence from base 1 to 14 in FIG. 1B) forms a double-stranded RNA (14-base pair) which represents the remaining a1-a2 stem structure from the folded precursor RNA template. In FIG. 4, band (b) migrated at around 82-bases, which is longer by 13-bases than band (a). Since the double-stranded RNA is resistant to RNase A and heating prior gel electrophoresis dissociated 14-base RNA from msDNA, the entire 5'-end arm remained with the DNA strand (see FIG. 3). Thus, band (a) and (b) products consist of 71- and 84-bases, respectively, which migrated at 69- and 82-base positions, respectively, in FIG. 4.

To unambiguously prove the existence of structure IVa, the band (b) product was extracted from the gel, and retreated with RNase A. As shown in FIG. 5, the purified band (b) product (lane 3) changed its mobility to the band (a) position in a sequencing gel when it was treated a second time with RNase A (lane 5). No change in the mobility was observed before and after RNase treatment of band (a) (lanes 4 and 6, respectively).

Interestingly, the size difference between band (d) and (c) in FIG. 4 is also approximately 13-bases; the size difference between band (d) and (b) or between band (c) and (a) is approximately 35-bases. On the basis of these sizes, the band (c) product is likely a result of further extension of the single-stranded DNA all the way to the branched G residue using the msdRNA as a template (see FIG. 3). This extension elongates the msDNA by another 35-bases at its 3'-end, which agrees well with the size of band (c). Such DNA elongation from the 3'-end of msDNA has been demonstrated for msDNA-Ec67 with a partially purified RT-Ec67 (Lampson et al., 1990). Thus the band (d) product is considered to consist of the fully extended msDNA strand (102-bases) plus the 17-base RNA similar to the RNA structure of the band (b) product (structure VIb in FIG. 3).

The above studies show the complementation in a cell-free system using the RNA fraction from cells harboring p67-BHO.6 and RT partially purified from cells harboring pRT-67. The cell-free synthesis of msDNA-Ec67 was initiated de novo by the bacterial RT and from the expected first base. The following features of the cell-free system of synthesis of the msDNAs described are particularly noteworthy: (1) The incorporation of the first dNTP for the primary reaction for msDNA-Ec67 as well as further extension of the DNA chain is absolutely dependent upon the addition of RT and the RNA fraction containing the transcript from the msr-msd region. If either of them was omitted from the reaction mixture, the specific incorporation of the first base (dTTP for the wild-type msDNA-Ec67) into the precursor molecule was not observed. (2) The first base linked to the precursor RNA molecule is determined by the 118th-base of the primary RNA transcript from the msr-msd region serving as a template (see FIG. 1C). For other msDNAs it is the base corresponding to that in the 118th position in this msDNA species. The first base is always complementary to the base at the 118th position of the precursor RNA molecule. (3) The 15th residue of the primary transcript is a G residue and is essential for the priming reaction. This G residue corresponds to the branched G residue of msDNA-Ec67 (see FIGS. 1B and 1C). In other msDNAs the G may be positioned at other positions as described. (4) The compound to which the first dNTP, determined by and complementary to the 118th-base in the primary transcript, is linked, is sensitive to RNase A and detected as a single band in acrylamide gels. From its mobility the compound appears to consist of 133-bases. (5) When all four dNTPs are added in the reaction mixture, the DNA chain is elongated and the major product from this reaction is estimated to consist of approximately 69-bases. (6) When ddNTPs are added in the elongation reaction in addition to four dNTPs, a sequencing ladder is formed, and the sequence read from the ladder completely matches with the DNA sequence of msDNA-Ec67. (7) The RNA molecule attached to the 5'-end of the extended DNA molecule is protected from RNase A digestion. This protection from RNase A is due to the formation of a double-stranded structure which represents the remaining a1-a2 stem structure from the folded precursor RNA molecule, and thus the RNA molecule can be digested if the cell-free product is incubated in a boiling water bath prior to RNase A treatment. (8) The size of RNA removed by the RNase A treatment after boiling is 13-bases.

The following Examples are given for purpose of illustration and not in any way by way of limitation on the scope of the invention.

EXAMPLE 1

The method of in vitro synthesis of msDNA in *M. xanthus* is described in detail in allowed U.S. patent application Ser. No. 07/315,427 and incorporated herein by reference.

EXAMPLE 2

The method of in vivo synthesis of msDNA-Ec67 in yeast is described in detail in pending patent application Ser. No. 07/753,110 and is incorporated herein by reference.

EXAMPLE 3

The method of in vivo synthesis of msDNA-Mx65 is described in detail in Dhundale, *Journal of Biological Chemistry*, 263, 9055–9058 (1988).

EXAMPLE 4

The method of in vivo synthesis of msDNA-Ec67 in *E. coli* is described in detail in U.S. patent application Ser. No. 07/315,432, which is incorporated herein by reference.

EXAMPLE 5

Figure 8A:
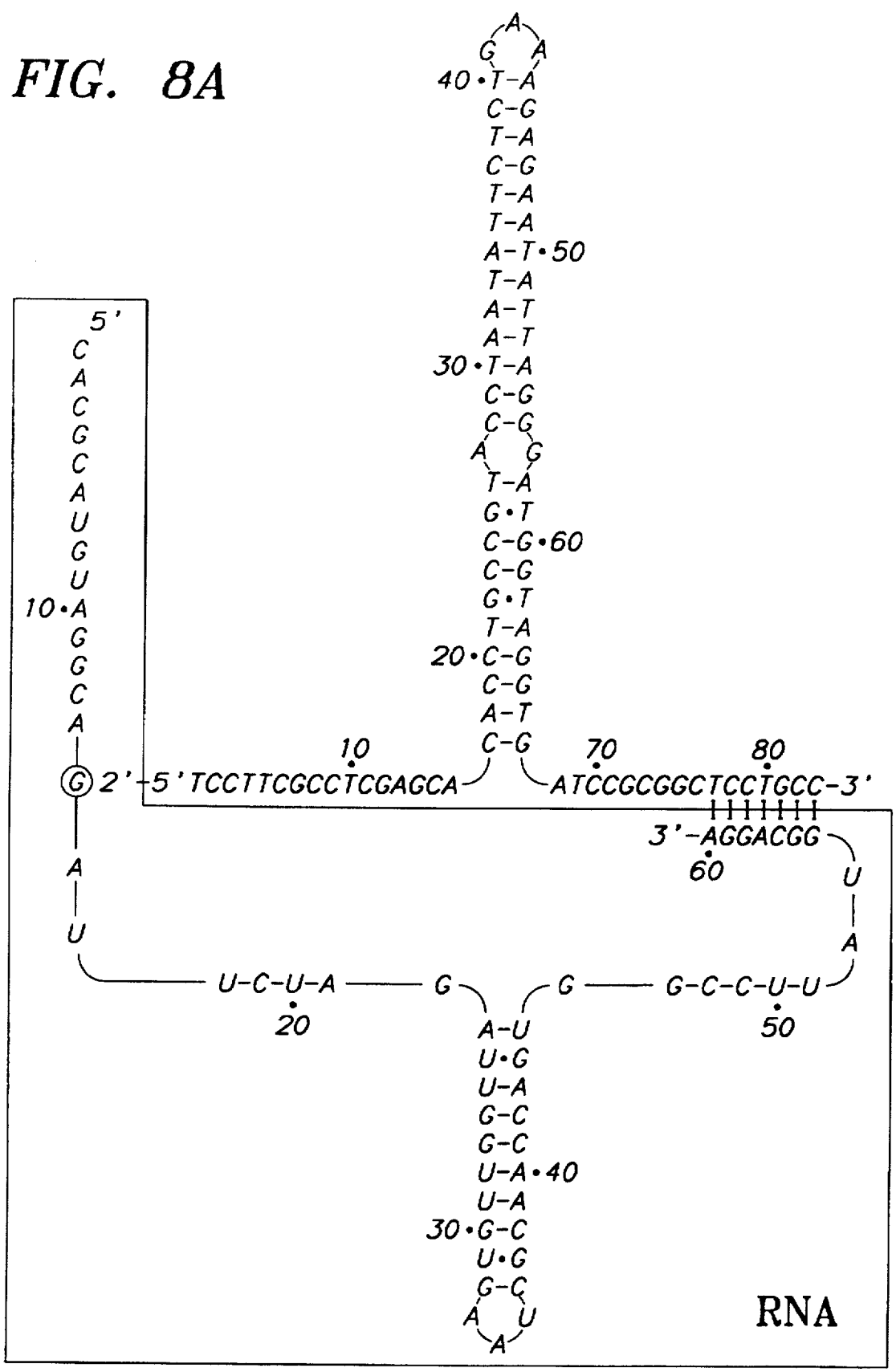
FIG. 8a (Seq ID Nos. 22 and 23) and 8b (Seq ID Nos. 24 and 25) show two other msDNAs, Ec100 and Ec101.
Figure 8B:
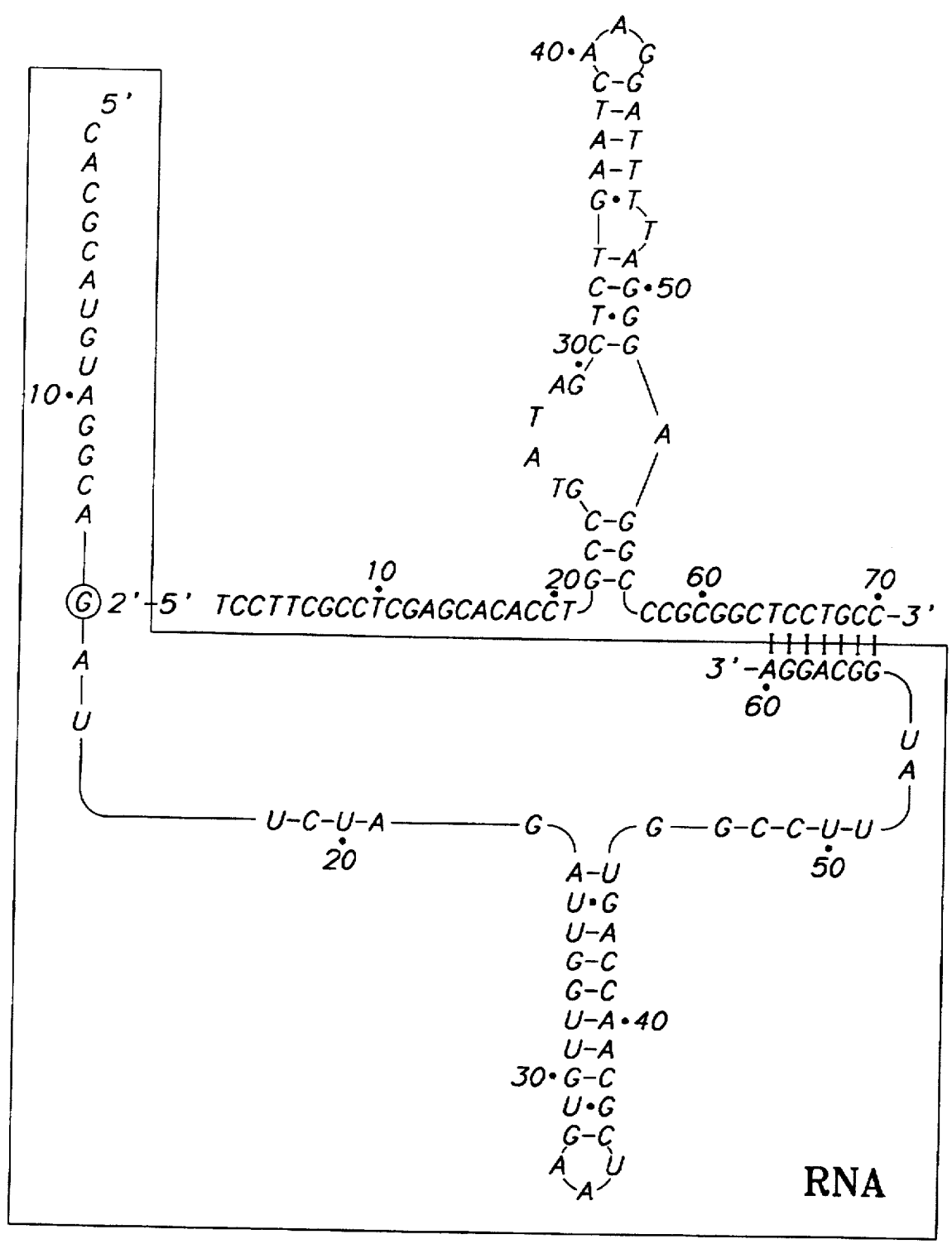
Figure 9A:
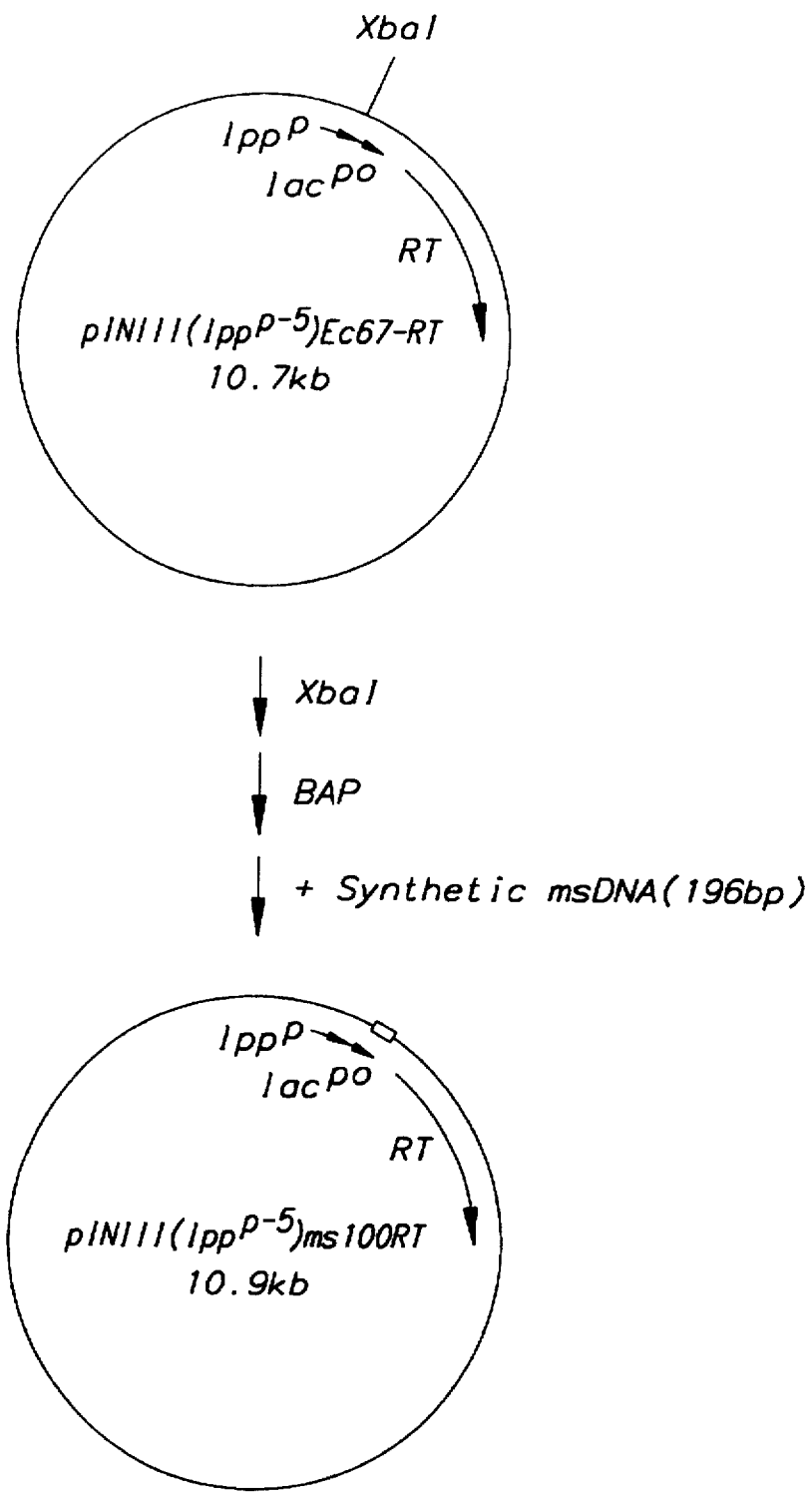
FIG. 9a shows the protocol for constructing synthetic msDNA 100.

Two separate synthetic msDNA molecules were constructed. A 196-bp synthetic msDNA containing an entire msr-msd region was synthesized from four double-stranded oligonucleotide units. The synthetic genes and their components are shown in FIG. 9b. Eight single-stranded oligonucleotides, forty-six to fifty-six bases in length were synthesized. The appropriate pairs of oligonucleotides were annealed by heating at 100° C. for 5 minutes, then cooled at 30° C. for 30 minutes and for 30 minutes at 4° C. An *E. coli* pINIII(lpp$^{p-5}$) expression vector retron was digested with XbaI-EcoRI, and an XbaI-EcoRI fragment from the clinical *E. coli* strain C1-1 was inserted such that the RT gene was under lpp-lac promoter control and used to transform *E. coli*. After identification of the clone, the 10.7-kb pINIII(lpp$^{p-5}$) Ec67-RT plasmid DNA was isolated. The 196-bp synthetic msDNA fragment was then inserted into the vector by digesting with XbaI, treating the vector ends with bacterial alkaline phosphatase and ligating the fragment into the site. The construction scheme is shown in FIG. 9. *E. coli* CL-83 was transformed with the pINIII(lpp$^{p-5}$) ms100-RT plasmid and msDNA was synthesized. This artificial msDNA was designated ms100 and is illustrated in FIG. 8a.

Following the method of Example 5, other msDNAs are synthesized from synthetic msDNAs containing the entire msr-msd region. An appropriate number of oligonucleotides of an appropriate size are selected. The oligonucleotides preferably have incorporated in their sequences restriction enzyme cleavage sites to facilitate insertion into a vector, as described below. Such oligonucleotides are commercially available. By known methods, such as the polymerase chain reaction (PCR), see Maniatis, the msr gene is synthesized. The same procedure is followed for the msd gene. Using appropriate number and sequence of oligonucleotides, the msd gene is synthesized. The msr and msd genes are annealed to one another at their respective 3' ends, with an overlap at the 5' ends. Thus, for the first time, the template for synthesizing msDNA, consisting of msr and msd genes, is obtained synthetically. In this specification, the msDNA so produced is referred to as "synthetic" because both parts of the hybrid msDNA molecule, the msr and the msd portions, are synthetic.

The annealed msr and msd genes so produced serve as a template to generate msDNA when reacted with an RT, such as a bacterial or yeast RT. The RT is isolated by known methods from any suitable bacterial source, such as the numerous bacterial sources known and described it the literature, including Myxococcus (for example *xanthus*), Escherichia (for example *coli*), Proteus, Klebsiella, FLexabacter, Stigmatella, and Salmonella.

A vector construct such as a plasmid, that is capable of producing msDNA from the synthetic template may be generated as follows. A retron from a suitable bacteria or yeast may be digested with restriction enzymes to produce a fragment containing the entire RT gene. The RT gene is then inserted into a competent vector, such as a plasmid, which gene may be under the control of an inducible promoter, such as the lac promoter.

The template containing the msr and msd genes is digested with an appropriate restriction enzyme and is then ligated into the vector containing the RT gene, either upstream or downstream of the RT. Conversely, the template may be ligated into the vector, followed by insertion of the RT gene. A suitable prokaryotic or eukaryotic cell, such as bacteria or yeast, is transformed with the vector and the transformed cell is allowed to produce the hybrid molecule, msDNA. An msDNA which conforms in structure with the generic msDNA structure described herein is then isolated by known procedures. These synthetic hybrid msDNA molecules are useful vehicles which may be used to carry antisense fragments, as described herein.

It is noteworthy that both components of the synthetic hybrid msDNA molecule, the msr and the msd components, are produced synthetically outside of an organism by known methods from oligonucleotides.

EXAMPLE 6

Figure 10:
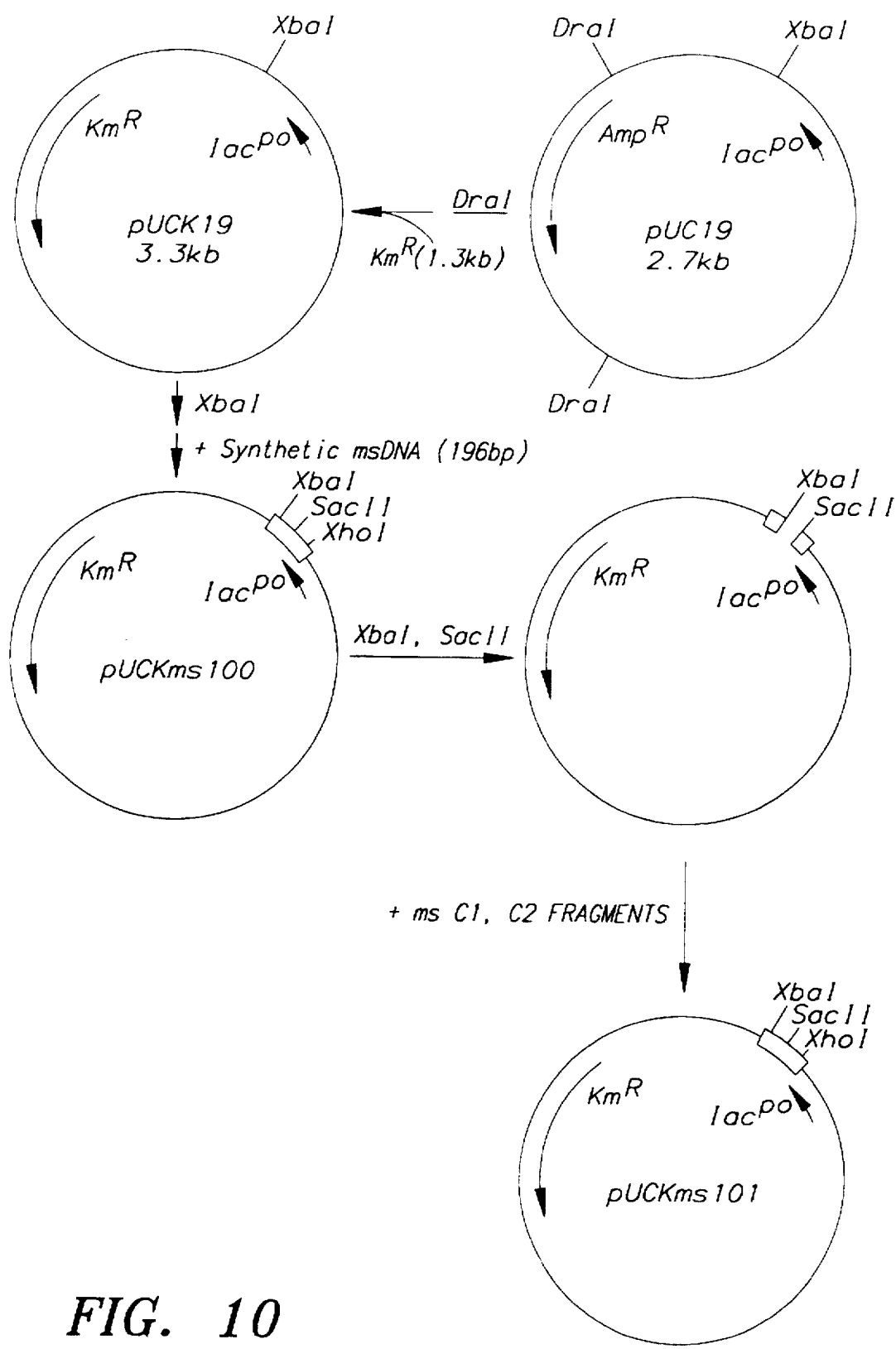
FIG. 10 shows the protocol for construction of msDNA 101.

A second synthetic msDNA, ms101, was expressed from the vector pUCK19, a derivative of pUC19. pUC19 DNA was digested with DraI and the 2-kb fragment was isolated. The isolated fragment was ligated to a 1.3-kb HinfI fragment from Tn5 encoding the kanamycin resistance gene. The resultant 3.3-kb plasmid, pUCK19, was digested with XbaI and the 196-bp synthetic msDNA described above in Example 9 was inserted. The pUCKms100 construct was digested with XhoI and SacII which results in the excision of a 61-bp fragment from within the ms100 region. A synthetic 45-mer double-stranded oligonucleotide (shown in FIG. 10 as ms-C1.2) was ligated into the vector yielding pUCKms101 in which the msr-msd region is under lac control. The construction scheme is shown in FIG. 10. RT was provided by transforming *E. coli* containing pUCKms100 or pUCKms101 with pINIII(lpp-$P^{-5}$) Ec67-RT. msDNA production was detected in the cells containing these constructs.

EXAMPLE 7

The ability of purified Ec67-RT to synthesize DNA from various templates composed of random sequences was examined using three different template:primer systems.

*E. coli* 5S rRNA was annealed to a synthetic 15-base oligo-DNA (15-mer) complementary to the 3' end of *E. coli* 5S rRNA which served as a primer for the polymerase. The 5S rRNA template:primer was prepared by mixing 30 pmoles of *E. coli* 5S rRNA (Boehringer Mannheim) with 120 pmoles of a synthetic 15-base, oligo-DNA (5'-ATCCCTGGCAGTTCC-3') (Seq ID No.36). The mixture was dried, then resolubilized in 30 μl of a formamide solution (80% formamide, 20 mM PIPES-pH 6.5, 0.4M NaCl). The solution was then heated at 90° C. for 10 minutes, transferred to 37° C. for 2 to 3 hours, followed by room temperature for 30 minutes. The annealed template:primer was then precipitated with ethanol and lyophilized.

Figure 11:
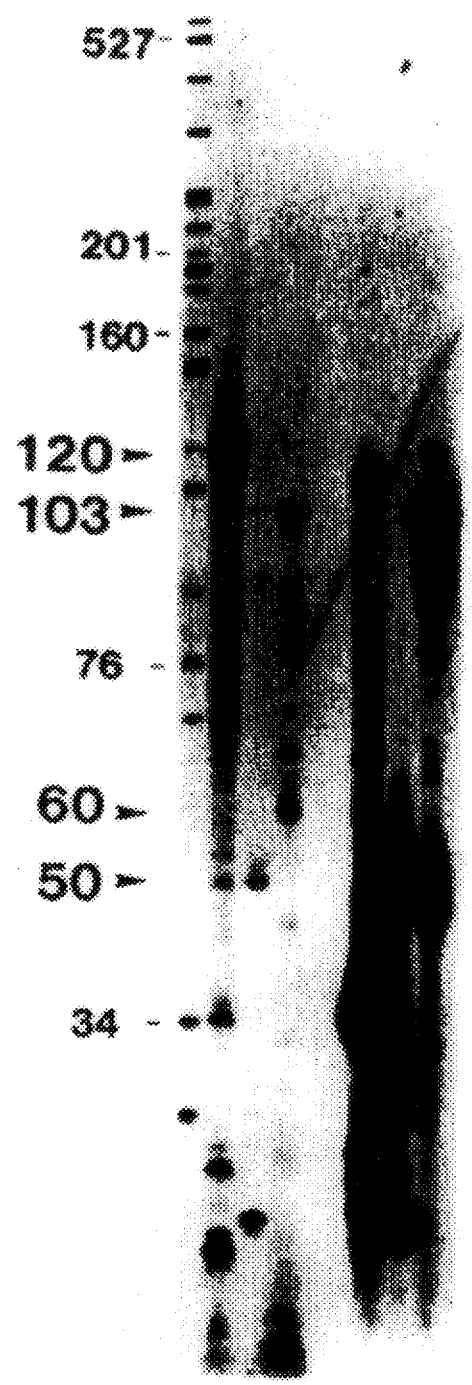
FIG. 11 shows cDNA production obtained from RNA or DNA templates.

The annealed template:primer was added to a reaction buffer (pH 7.8) containing dNTPs and [α-$^{32}$P]dCTP. An aliquot from the glycerol gradient fraction containing the purified Ec67-RT was added to the reaction mixture and incubated at 37° C. for 15 minutes. The products were treated with RNase A before analysis by gel electrophoresis. Complete extension of DNA synthesis from the 3' end of the primer, using 5S rRNA as a template, should give a DNA product of 120 nucleotides. FIG. 11, lane 1 shows the labeled products formed by the Ec67-RT after electrophoresis on a 6% polyacrylamide sequencing gel. A predominant band migrated at about 120 bases which was resistant to treatment with RNase A. A band of similar size was also produced when Avian Myeloblastosis virus-reverse transcriptase (AMV-RT) was substituted for the bacterial enzyme in the reaction mixture (arrow, FIG. 11, lane 4). Although there are several intermediate size products formed, the bacterial enzyme, like the retroviral polymerase, synthesized a full length cDNA of 120 bases using the 5S rRNA as a template with a 15-mer DNA as a primer.

The Ec67-RT also polymerized DNA using DNA as a template. In this reaction a 50-base, synthetic DNA was annealed to a synthetic 20-mer DNA primer complementary to its 3' end. The synthetic 50-base oligo-DNA template (5'-CGGTAAAACCTCCCACCTGCGTGC-TCACCTGCGTTGGCACACCGGTGAAA-3') (Seq ID No. 37) was annealed to a complementary, 20-base oligo-DNA primer (5'-TTTCACCGGTGTGCCAA-3') (Seq ID No. 38) in a similar manner. Total RNA prepared from 1.2 mls of an overnight culture of *E. coli* C2110/pC1-1EP5b was used for a reaction in which msDNA served as a template:primer. RNA was prepared by the hot phenol method.

This oligo-DNA template:primer was allowed to react with the Ec67-RT and the resulting products formed are shown in FIG. 9, lane 2. A small band appears at the bottom of lane 3, migrating at about 20-bases in size. This indicates that only one to three dNTPs have been added to the 20-base primer since the first and third bases extending from the 3' end of the primer would be expected to incorporate the labeled dCTP resulting in this small product. A larger, but weakly labeled band is also present at roughly 50-bases in size (arrow, FIG. 9). This product was resistant to treatment with RNase A and was the size expected for a complementary DNA extending the full length of the 50-base template. A heavily labeled band of similar size is also produced when AMV-RT is substituted for the bacterial enzyme in the reaction (FIG. 9, lane 5). The ability of the Ec67-RT to synthesize a full length cDNA from either the 5S rRNA template or the oligo-DNA template is dependent on a primer annealed to the template.

The lanes in FIG. 11 were as follows: Lane S, pBR322 digested with MspI and $^{32}$P-labeled with the Klenow fragment; lane 1, cDNA products synthesized when Ec67-RT is added to the reaction mixture containing *E. coli* 5S rRNA as template, annealed to a complementary synthetic 15-mer DNA as a primer; lane 2, Ec67-RT plus a 50-base, synthetic DNA as a template annealed to a 20-mer DNA primer; lane 3, Ec67-RT plus total RNA from *E. coli* C2110/pC1-1EP5b containing msDNA-Ec67 as a template:primer. Lanes 4, 5, and 6 are the same reactions as those in lanes 1, 2, and 3, respectively, except that AMV-RT was substituted for Ec67-RT in the reaction mixture. Reactions with AMV-RT were diluted 100-fold before loading on the gel.

Likewise, the other RTs disclosed herein are capable of synthesizing cDNAs from either a DNA or an RNA template.

EXAMPLE 8

The msDNAs of the invention can be additionally synthesized in vitro in a cell-free system. msDNA-Ec67 was synthesized de novo when RT-Ec67 and a total RNA fraction containing the primary transcript from the msr-msd region of retron-Ec67 were isolated, mixed and incubated in the presence the of 4 dNTPs at a temperature suitable for the reaction (preferably physiological temperatures) in the presence of buffers. To remove a 5' end of the RNA transcript, the reaction product is incubated with RNase A. The detailed experimental protocol is hereinafter described.

Bacterial Strains and Culture Media—*E. coli* SB221 (Nakamura et al., 1982) and C2110 (his rha polA1) were used. These *E. coli* cells harboring plasmids were grown in L-broth (Miller, 1972) in the presence of ampicillin (50 µ/ml) or spectinomycin (50 µg/ml).

Plasmid Construction and Mutant Isolation—To express the msr-msd region from retron-Ec67, the BssHII site at the base number from 181 to 186 (see FIG. 6 in Lampson et al., 1989b) was changed to a BamHI site by inserting an 8-mer-BamHI linker at the blunt-ended BssHI site. Subsequently, the 615-bp BamHI-HindIII (base number from 795 to 800 in FIG. 6 in Lampson et al., 1989b) was isolated. This fragment consists of the msr-msd region with its own promoter and a 5' end portion of the RT gene (encoding the N-terminal 126-residues out of the 586 residue RT-Ec67), which was then cloned into the BamHI-HindIII sites of pSP65 (Boehringer Mannheim). The resulting plasmid was designated p67-BHO.6. In order to purify RT-Ec67, the RT gene was cloned under the lpp-lac promoter. For this purpose, an XbaI site was first created 13 bases upstream of the RT initiation codon by oligonucleotide-directed site-specific mutagenesis (Inouye and Inouye, 1991); TCTG (base 410 to 404 in FIG. 6 in Lampson et al., 1989b) changed to TCTAGA (see FIG. 1A in Lampson). Then, the resulting 3.3-kilobase (kb) XbaI-EcoRI fragment was cloned into the XbaI-EcoRI sites of pGB21pp-$p^{r-5}$ which was constructed by cloning the 1-kb PstI-BamHI fragment from pINIIIlpp$^{r-5}$ (Inouye and Inouye, 1985) into the PstI-BamHI sites of pGB2 (Churchward et al., 1984). The resulting plasmid was designated pRT-67. Various msd-msr mutations were isolated by oligonucleotide-directed site-specific mutagenesis (Inouye and Inouye, 1991) using p67-BHO.6 (FIG. 1A). Oligonucleotides used are: 5' TGCGAAGGTGTGCCT-GCA$^3$' (Seq ID No. 39)for mutation 1 (A to T at position 118 in FIG. 1C), TGCGAAGGGGTGCCTGCA (seq ID No. 40) for mutation 2 (A to G at position 118 in FIG. 1C), ATGTAGGCAAATTTGTTGG (Seq ID No. 41) for mutation 3 (branched G to A at position 15 in FIG. 1C), and TGCGAAGGAATGCCTGCAT (Seq ID No. 42) for mutation 4 (G to A at position 119 in FIG. 1C).

Purification of RT-Ec67—The RT (from Ec67) was purified by the method described by Lampson et al., *Science*, 243, 1033–1038 (1989b) (see also, Lampsonetal., *J. Biol. Chem.*, 265, 8490–8496 (1990)) from C2110 harboring pRT-67 with some modifications. After DEAE-cellulose batch purification, the sample was applied to a Mono Q column (5 mm×50 mm). Elution was carried out with a linear gradient of NaCl from 250 mM to 1M using a Pharmacia FPLC system. The RT activity was eluted between 320 mM and 350 mM NaCl and separated.

Isolation of the RNA Transcript from the msr-msd Region—Total RNA fraction was isolated from SB221 cells harboring p67-BHO.6 with the method described by Chomzynski and Sacchi (1987). This fraction containing the transcript from the msr-msd region was used as the template for msDNA synthesis in the cell-free system.

Cell-free System for msDNA Synthesis—To produce msDNA, a total RNA fraction from a 1-ml culture was added to a 10 µl reaction mixture containing RT buffer (50 mM Tris-HCl (pH 8.3), 1 mM dithiothreiol, 40 mM KCl, 6 mM MgCl$_2$) and 2 µCi ($\alpha$-$^{32}$P)dTTP and 2.5 mM each DATP, dGTP and dCTP were added. The reaction was started by adding 2 µl of the Mono Q-purified RT fraction. The mixture was incubated at 37° C. for 30 minutes. The samples were analyzed by electrophoresis on a 6% acrylamide in 9M urea followed by autoradiography.

Dideoxy Sequence Analysis during DNA Extension—A total RNA fraction prepared from a 25-ml culture was added to a 100 µl reaction mixture containing 100 µCi of |$\alpha$-$^{32}$P| dTTP and 20 µl of the Mono Q purified RT fraction in RT buffer. After incubating at 37° C. for 5 minutes, the reaction mixture was divided into five tubes (20 µl each). Four tubes were used for individual chain termination reaction using 14 µl of the termination mixture of DNA sequencing with Sequenase (United States Biochemical Corp.). After the reaction mixtures were incubated at 37° C. for 15 minutes, 0.5 µl of RNase A (10 mg/ml) and 1.3 µl of 0.25M EDTA were added to each reaction mixture and the mixture was incubated for another 5 minutes. The reaction mixture was extracted with phenol, and then with chloroform. The reaction products were precipitated by ethanol, which were then solubilized in 6 µl of sample buffer (32% formamide, 6.7 mM EDTA, 0.017% BPB and XC). The solubilized samples were heated at 95° C. for 2 minutes. The msDNA is separated and analyzed by a 10% sequencing gel.

By the procedure described above, other msDNAs can be synthesized in a similar manner from an RNA fragment carrying the msr-msd encoding region and the RTs.

EXAMPLE 9

FIG. 12 shows the structures of msDNA-Ec73 and its derivatives, and the Antisense Sequences used in the msD-NAs. FIG. 12*a* shows the msDNA-Ec73 isolated from clinical *E. coli* strain Cl-23 (*Cell*, vol. 37, pages 429–436). FIG. 12*b* shows the msDNA-miniEc73 constructed by deleting 43 bases (from C-15 to G-57) from the DNA structure of msDNA-Ec73. FIG. 12*c* and *d* show the msDNA-anti-lppN25 and msDNA-anti-lppN34, derivatives of msDNA-Ec73 containing anti-lpp sequences a and b (FIG. 12*f*) in the loop structure, respectively. FIG. 12*e* shows the msDNA-anti-lppE25, a derivative of msDNA-Ec73 containing anti-lpp sequence a (FIG. 12*f*) with an EcoRI site at the stem region. The anti-lpp sequences are circled. Boxes enclose msdRNA, and the branching G residues are circled. FIG. 12*f* shows the 5'-end ribosomal-binding region of the lpp mRNA and the nucleotide sequences of antisense DNA a (25 bases) and b (34 bases). The initiation codon, AUG, of the lpp gene is boxed and Shine-Dalgarno sequence is indicated by dots.

EXPERIMENTAL PROCEDURES

Bacterial Strains and Plasmids—*E. coli* strain JA221/F+ lacIq (*Cell*, vol. 37, pages 429–436) was used for the expression of msDNAs. For the internal cleavage of an EcoRI site in msDNA-anti-lppE25, *E. coli* MM294 (*J. Biol. Chem.*, vol. 256, pages 2143–2153) was used. Strain MM294 was transformed with pJREcoRI containing the gene for endonuclease EcoRI and the gene for EcoRI methylase. These two genes were obtained from pGJ440 (Id.) by digesting the plasmid DNA with BsaAI and ScaI. The resulting 2.1-kb fragment was inserted into the unique HincII site of a low copy plasmid, pCL1921 (spcr) (*Nucleic Acids Res.*, vol. 18, page 4631). For the expression of msDNA, a pINIII (lppp-5) vector (*Nucleic Acids Res.*, vol. 13, pages 3101–3110) was used.

Construction of Plasmids for the Induction of Antisense msDNAs—The pINIII(lppp-5) vectors containing anti-lpp sequences were constructed as follows: first to introduce a NcoI or an EcoRI site in the msd region and delete 56 bases in the upper portion of msDNA-EC73, a two-step PCR was performed using a pT7Ec73 msr-msd (*J. Biol. Chem.*, vol. 270, pages 581–588) as a template. In the first PCR, two sets of primers were used, 5'AATCTAGACAGAGCCAAAC-CTAG3' (Seq. ID No. 43) (oligo 5641) corresponding to base 10411 to 10425 and 5'TACTTGAGCAGGCAT-AGCTAA3' (Seq. ID No. 44) (oligo 5790; the boxed sequence is the NcoI site) complementary to base 10479 to 10489 and 10546 to 10556, and containing 6 bases for NcoI site in the middle: 5'TCTCTAGATCCTTATGCACCT-TGA3' (Seq. ID No. 45) (oligo 5640) complementary to base 10672 to 10689 and oligo 5791 which is a complementary sequence of oligo 5790. The second PCR was performed using the amplified fragments, and oligos 5641 and 5640 as primers which created an XbaI site at their 5' and 3' ends. The amplified fragments were cloned into the XbaI site of pINIII(lppp-5)A1 (*Nucleic Acids Res.*, vol. 13, pages 3101–3110) of which the EcoRI site was eliminated. Double-stranded oligonucleotides consisting of anti-lpp sequences a and b in FIG. 12*f* with NcoI sites at the ends were synthesized and cloned into the NcoI site of pINIII (lppp-5)msDNA/NcoI, resulting in pINIII(lppp-5)N25 for msDNA-anti-lppN25 (FIG. 12*c*) and pINIII(lppp-5)N34 for msDNA-anti-lppN34 (FIG. 12*d*) respectively. In the case of construction of pINIII(lppp-5)E25 for the production of msDNA-anti-lppE25 (FIG. 12*e*), pINIII(lppp-5)msDNA/ EcoRI was constructed with the same procedure used for pINIII(lppp-5)N25. To make sure EcoRI enzyme is able to digest the EcoRI site formed on a stem of msDNA, 3 bases were added at the 5'-end and 3'-end of EcoRI site as shown in FIG. 12*e*. After confirming the DNA sequence of the constructs, the 0.95-kb BamHI fragment carrying msDNA Ec73 reverse transcriptase (RT-Ec73) from pUC7XbaI73RT (*J. Biol. Chem.*, vol. 270, pages 581–588) was inserted at the BamHI site of these plasmids and the orientation of RT-Ec73 was determined by restriction digests.

RESULTS AND DISCUSSION

Production of msDNA containing Antisense DNA against the lpp mRNA—By deleting a substantial central part of the msDNA-coding region (msd) of Retron RT-Ec73, a retron responsible for msDNA-miniEc73 (FIG. 12*b*) was constructed using a pUC vector (*Gene*, vol. 19, pages 259–268). This msDNA consists of 30 nucleotides, 43 nucleotides shorter than msDNA-Ec73 (FIG. 12*a*). When this plasmid was cotransformed with pRT-73 (*J. Biol. Chem.*, vol. 268, pages 2684–2692), the yield of msDNA miniEc73 in the presence of 1 mM isopropyl-■-D-thiogalactopyranoside was as high as that of msDNA-Ec73, estimated at a level of 5000 copies/cell.

Because at least the upper part of the stem-loop structure of msDNA-Ec73 can be replaced, we added new sequences at the loop region of the msDNA-miniEc73. For this purpose, the entire stem-loop region was replaced with a NcoI site. This allowed insertion of sequences a and b (FIG. 12*f*) to produce msDNA-anti-lppN25 (FIG. 12*c*) and -anti-lppN34 (FIG. 12*d*), respectively. In these msDNAs, the loop sequences are complementary to the translation initiation region of the mRNA for the major outer membrane lipoprotein, the most abundant protein in *E. coli*. The protein was used as a target for antisense RNA regulation (*Cell*, vol. 37, pages 429–436). Similarly, another artificial retron was constructed to produce msDNA-anti-lppE25 (FIG. 12*e*). This msDNA is similar to msDNA-anti-lppN25 except that it has a longer stem so that when an EcoRI site is recreated upon the formation of the msd stem structure in the msDNA, it can be digested by EcoRI enzyme.

All the artificial retrons were constructed in the pINIII (lppp-5) vector (*Nucleic Acids Res.*, vol. 13, pages 3101–3110) as in the case of msDNA-mini Ec73 so that msDNA productions were inducible by IPTG, a lac inducer. FIG. 13 shows the production of msDNAs containing Anti-lpp sequences. msDNAs were isolated from 5-ml cultures of JA221/F'lacIq (*Cell*, vol. 37, pages 429–436) harboring pINIII(lppp-5)N25 (lanes 2 and 3), pINIII(lppp-5)N34 (lanes 4 and 5), and pINIII(lp pp-5)E25 (lanes 7 and 8). Lanes 1 and 2 were JA221/F'lacIq without a plasmid. MW is the HaeIII-digested pBR322 DNA and numbers on the left indicate the number of bases. msDNAs were isolated by the alkali-SDS method described by Lampson et al (*Science*, vol. 243, pages 1033–1038), treated with RNase A (25 μg/ml) for 10 min at 37° C. and then analyzed by 8% polyacrylamide gel electrophoresis. Cells growing in M9 medium were induced with 1 mM IPTG at a Klett unit of 30 and harvested at a Klett unit of 150 to isolate msDNA.

As shown in FIG. 13, the amounts of msDNA detected in the late logarithmic growth were somewhat different in three constructs possibly due to their stabilities. msDNA-anti-lppN25 was produced at the highest level and estimated as approximately 5000 copies/cell. Multi-bands on nondenatured gels as shown in FIG. 2, became a single band when they were analyzed on denatured gels after labeling at their 3'-ends. This result indicates that the multi-bands appeared due to different conformations of msDNA.

Effects of Antisense DNA on the lpp Expression—The effects of the antisense DNA was examined on the production of the *E. coli* major outer membrane lipoprotein. FIG. 14 shows the inhibition of lipoprotein production by antisense DNA.

One ml of the same cultures used in FIG. 13 were labeled with 5 μCi of Trans35S label (Amersham) for 10 min at a Klett unit of 150. Membrane fractions were isolated by the method described previously (*Cell*, vol. 37, pages 429–436) and analyzed by 17.5% SDS-polyacrylamide gel electrophoresis. Lanes 1 and 2, JA221/F'lacIq; lanes 3 and 4, JA221/F'lacIq harboring pINIII(lppp-5)N25; lanes 5 and 6, harboring pINIII(lppp-5)N34 and; lanes 7 and 8, harboring pINIII(lppp-5)E25. Lanes 2,4,6 and 8 were treated with 1 mM IPTG. The lipoprotein was quantitated using an Imaging Densitometer Model GS-670 (Bio-Rad Laboratories) by comparing the density of the lipoprotein to the density of OmpA indicated by an arrow with the letter A.

In the presence of 1 mM IPTG, significant inhibition was detected in all the constructs (75% for N25, lane 4; 70% for N34, lane 6; and 77% for E25, lane 8 in FIG. 14).

EcoRI Digestion of msDNA inside the Cell—In msDNA anti-lppE25, an EcoRI site was designed to be present in the stem region of the msDNA. If the proposed structure in FIG. 12*e* is formed, the msDNA should be digested by EcoRI. When the msDNA extracted from the cells and purified by polyacrylamide gel electrophoresis were digested by EcoRI, three single-stranded DNA fragments were obtained in expected sizes:46 bases, from 12 to 48; 16 bases from 49 to 65, and 11 bases from 1 to 11 of msDNA-anti-lppE25 (FIG. 12*e*). The result indicates that the msDNA molecules indeed form the secondary structure shown in FIG. 12*e*. Next, to generate a short single-stranded DNA inside cells, msDNA anti-lppE25 was transformed into *E. coli* strain MM294 which was expressing the EcoRI enzyme as well as the EcoRI methylase. In this cell, the chromosomal DNA is protected from EcoRI digest because of the methylation at the EcoRI sites (*J. Biol. Chem.*, vol. 256, pages 2143–2153). However, since the EcoRI site on the msDNA is formed as a result of annealing of the unmethylated single-stranded DNA synthesized by RT, the EcoRI site should be still susceptible to EcoRI cleavage. No intact msDNA was detected indicating that the msDNA was indeed digested by EcoRI. This result indicates that msDNA is a potential vector to release shorter single-stranded oligodeoxyribonucleotides.

There is cofiled herewith as part of the application, a manuscript entitled "Gene Regulation By Antisense DNA Producted In Vivo", by Mao, et. al., which manuscript is incorporated fully herein by reference.

While preferred embodiments of the present invention have been described herein, it will be understood that various changes and modifications may be made without departing from the spirit of the invention and these are intended to be within the scope of the claims.

REFERENCES

Antisense Research and Development, 1, 207–217 (1991), "Meeting Report: Gene Regulation by Antisense RNA and DNA", meeting review by Case and Dhundale (Hawkins and Krieg, Editors; Mary Ann Liebert, Inc., Publishers) and "A Listing of Antisense Patents, 1971–1991" page 219
BRL Catalogue, page 17 (1985)
Chomezynski and Sacchi, Analytical Biochemistry, 162, 156–159 (1987)
Churchward et al., Gene, 31, 165–171 (1984)
Current Protocols in Molecular Biology, Vol. 1 ("Protocols"), Units 3.7.1–3.7.2
Dhundale, Cell, 51, 1105–1112 (1987)
Dhundale, Journal of Biological Chemistry, 263, 9055–9058 (1988)
Hirashima et al., Proc. Natl. Acad. Sci. USA, 83, 7726–7730 (October 1986)
Houts, G. E., Miyagi, M., Ellis, C., Brand, D., and Beard J. W. (1979), J. Virol. 29, 517
Hsu et al., manuscript submitted to JBC entitled "Cell-free Synthesis of the Branched RNA-linked msDNA from Retron-Ec67 of Escherichia coli"
Inouye, Gene, 72, 25–34 (1988)
Inouye and Inouye, Directed Mutagenesis: A Practical Approach (McPherson, ed.) 181, Oxford University Press, New York (1991)
Inouye and Inouye, Nucleic Acids Res., 13, 3101–3110 (1985)
Lampson et al., Cell, 56, 701–707 (1989a)
Lampson et al., J. Biol. Chem., 265, 8490–8496 (1990)
Lampson et al., Science, 243, 1033–1038, (1989b)
Lease and Yee in JBC, 266, 14497–14503 (August 1991)
Lim and Maas, Cell 56, 891–904 (Mar. 10, 1989)
Marcus et al., J. Virol., 14, 853 (1974)
Miller, J. H., Experiments in Molecular Genetics (3rd. ed.), 433, Cold Spring Harbor Laboratory, Cold Spring Harbor, N.Y. (1972)
Molecular Cloning: A Laboratory Manual ("Maniatis") pages 129–130 and 213–216
Molecular Cloning: A Laboratory Manual ("Sambrook"), Vol. 1, Units 4.33–4.38
Molecular Cloning: A Laboratory Manual ("Sambrook"), Vol 1, Units 5.34, 5.52-5.55; Units 7.79–7.83; Vol. 2, Units 8.11–8.13, 8.60–8.63, 14.20–14.21 and 10.13 (and B1.26)
Nakamuraetal et al., J. Appl. Mol. Geneti., 1, 289–299 (1982)
Roth et al., J. Biol. Chem., 260, 9326–9335 (1985)
Sanger et al., Proc. Natl. Acad. Sci. USA, 74, 5463–5467 (1977)
Science, 252, 1374–1375 (Jun. 27, 1991), "Triplex DNA Finally Comes of Age"
Verma, I. M., The Enzymes, Vol. 14A (P. D. Boyer, ed.), 87–104, Academic Press, New York, (1977)
Weiner et al., Ann. Rev. Biochem 55, pp. 631–661 (1986)
Yee et al., Cell 38, pp. 203–209 (1984)

What is claimed:
1. A molecule which has features as shown below

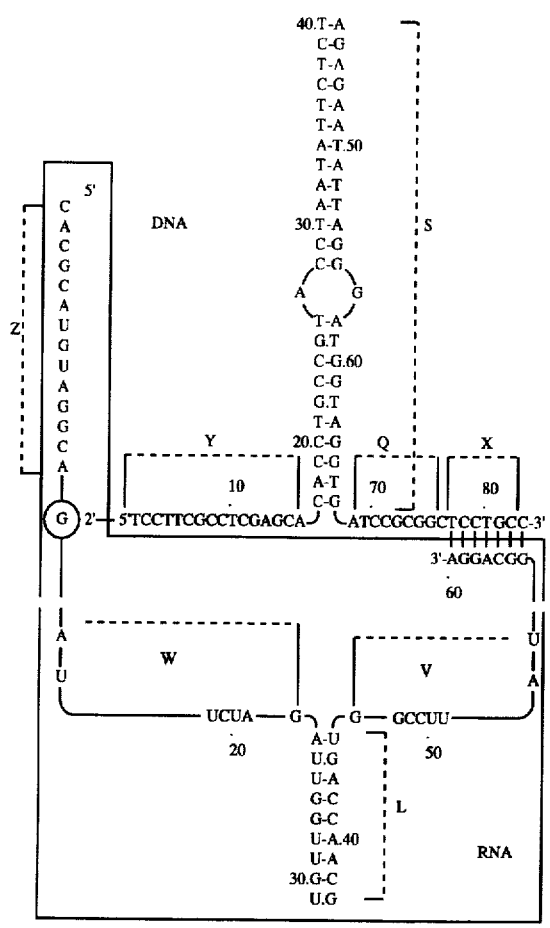

wherein X is 5 to 11 nucleotides in length, Y is 7 to 69 nucleotides in length, Z is 3 to 19 nucleotides in length, L is 9 to 26 nucleotides in length, S is 34 to 136 nucleotides in length, and the total nucleotide length of W, V, and Q is between 114 and 239 minus the sum of X, Y, Z, L, and S, wherein the DNA portion of the molecule has one stem-and-loop structure and the RNA portion of the molecule has at least one stem-and-loop structure, wherein said lengths are determined in number of nucleotides, which molecule has in its RNA portion a foreign DNA or RNA sequence.

2. The molecule of claim 1 wherein there are two stem-loop structures in the RNA portion.

3. A method for synthesizing a hybrid molecule which molecule comprises a single-stranded RNA covalently linked to a single-stranded DNA by a 2',5'-phosphodiester bond between the 2'-OH group of an internal rG residue and the 5'-phosphate of the DNA strand and non-covalently linked to the DNA by overlapping complementary nucleotides at the 3' ends of the RNA and DNA strands, which RNA and DNA portions each form a secondary structure, which method comprises:

a) transforming a bacterium or a yeast with a plasmid containing a gene for reverse transcriptase and a template for the reverse transcriptase (RT), which template has msr and msd genes, which msr and msd genes are annealed at their 3' ends to each other, b) allowing the bacterium or yeast to synthesize the hybrid molecule, and c) isolating the synthetic hybrid molecule so produced.

4. The method of claim 3 which, prior to synthesis of the hybrid molecule, comprising the msr and msd genes from oligonucleotides, and annealing the 3' ends of the genes to each other, thus obtaining a template for the RT.

5. The method of claim 3 wherein the RT gene is under the control of an inducible promoter.

6. The method of claim 3 wherein the template is upstream of the RT gene in the plasmid.

7. A method for synthesizing a hybrid molecule which molecule comprises a single-stranded RNA covalently linked to a single-stranded DNA by a 2',5'-phosphodiester bond between the 2'-OH group of an internal rG residue and the 5'-phosphate of the DNA strand and non-covalently linked to the DNA by overlapping complementary nucleotides at the 3' ends of the RNA and DNA strands, which RNA and DNA portions each form a secondary structure, which method comprises:

a) synthesizing an msr gene and an msd gene from oligonucleotides, b) annealing the msr and msd genes at their respective 3' ends, thereby obtaining a template for a reverse transcriptase, d) inserting the template and a gene for a bacterial reverse transcriptase (RT) into a plasmid, c) transforming a bacterium or a yeast with the plasmid, d) allowing the bacterium or yeast to produce the hybrid molecule, and e) isolating the synthetic hybrid molecule so produced.

8. An isolated hybrid molecule which comprises a single-stranded RNA portion covalently linked to a single-stranded DNA portion by a 2',5'-phosphodiester bond between the 2'-OH group of an internal rG residue and the 5'-phosphate of the DNA portion and non-covalently linked to the DNA portion by overlapping complementary nucleotides at the 3' ends of the RNA and DNA portions, which RNA and DNA portions each form a stem-loop structure, wherein the number of nucleotides in the DNA portion is between 67 and 162.

9. The hybrid molecule of claim 8 wherein there is one stem-loop structure in the DNA portion and at least one stem-loop structures in the RNA portion.

10. The hybrid molecule of claim 8 wherein the RNA portion has two stem-loop structures.

11. The hybrid molecule of claim 8 wherein the number of nucleotides in the RNA portion is between 49 and 82.

12. The hybrid molecule of claim 8 wherein the number of overlapping complementary nucleotides at the 3' ends of the RNA and DNA portions is between 5 and 11.

13. The hybrid molecule of claim 8 which has in its DNA or RNA portion a foreign DNA or RNA sequence which is an antisense sequence with respect to an mRNA of a target protein.

14. The molecule of claim 1 wherein the foreign DNA or RNA sequence is an antisense molecule with respect to an mRNA of a target protein.

15. A hybrid molecule which comprises a single-stranded RNA portion covalently linked to a single-stranded DNA portion by a 2',5'-phosphodiester bond between the 2'-OH group of an internal rG residue and the 5'-phosphate of the DNA portion and non-covalently linked to the DNA portion by overlapping complementary nucleotides at the 3' ends of the RNA and DNA portions, which RNA and DNA portions each form a stem-loop structure, and a foreign DNA or RNA sequence in the DNA or RNA portion.

16. The hybrid molecule of claim 15 wherein there is one stem-loop structure in the DNA portion and at least one stem-loop structures in the RNA portion.

17. The hybrid molecule of claim 15 wherein the RNA portion has two stem-loop structures.

18. The hybrid molecule of claim 15 wherein the number of nucleotides in the DNA portion is between 65 and 163.

19. The hybrid molecule of claim 15 wherein the number of nucleotides in the RNA portion is between 49 and 82.

20. The hybrid molecule of claim 15 wherein the number of overlapping complementary nucleotides at the 3' ends of the RNA and DNA portions is between 5 and 11.

21. The hybrid molecule of claim 15 which is isolated.

22. A hybrid molecule which comprises a single-stranded RNA portion covalently linked to a single-stranded DNA portion by a 2',5'-phosphodiester bond between the 2'-OH group of an internal rG residue and the 5'-phosphate of the DNA portion and non-covalently linked to the DNA portion by overlapping complementary nucleotides at the 3' ends of the RNA and DNA portions, which RNA and DNA portions each form a stem-loop structure, and a foreign DNA or RNA sequence in the DNA or RNA portion, which foreign DNA or RNA sequence is an antisense sequence with respect to an mRNA of a target protein.

23. The hybrid molecule of claim 22 wherein there is one stem-loop structure in the DNA portion and at least one stem-loop structures in the RNA portion.

24. The hybrid molecule of claim 22 wherein the RNA portion has two stem-loop structures.

25. The hybrid molecule of claim 22 wherein the number of nucleotides in the DNA portion is between 65 and 163.

26. The hybrid molecule of claim 22 wherein the number of nucleotides in the RNA portion is between 49 and 82.

27. The hybrid molecule of claim 22 wherein the number of overlapping complementary nucleotides at the 3' ends of the RNA and DNA portions is between 5 and 11.

28. The hybrid molecule of claim 22 which is isolated.

* * * * *